United States Patent
Ishiguro et al.

(10) Patent No.: US 9,772,224 B2
(45) Date of Patent: Sep. 26, 2017

(54) INFORMATION ACQUISITION APPARATUS AND INFORMATION ACQUISITION METHOD

(71) Applicant: Seiko Epson Corporation, Tokyo (JP)

(72) Inventors: Hideto Ishiguro, Shiojiri (JP); Tsukasa Eguchi, Matsumoto (JP); Hitoshi Tsuchiya, Suwa (JP); Megumu Ito, Suwa (JP)

(73) Assignee: Seiko Epson Corporation (JP)

( * ) Notice: Subject to any disclaimer, the term of this patent is extended or adjusted under 35 U.S.C. 154(b) by 0 days.

(21) Appl. No.: 15/041,617

(22) Filed: Feb. 11, 2016

(65) Prior Publication Data

US 2016/0238445 A1 Aug. 18, 2016

(30) Foreign Application Priority Data

Feb. 18, 2015 (JP) .................................. 2015-029301

(51) Int. Cl.
| | |
|---|---|
| *G01J 1/44* | (2006.01) |
| *A61B 5/1495* | (2006.01) |
| *A61B 5/00* | (2006.01) |
| *A61B 5/1455* | (2006.01) |
| *A61B 5/024* | (2006.01) |

(Continued)

(52) U.S. Cl.
CPC ............ *G01J 1/44* (2013.01); *A61B 5/02416* (2013.01); *A61B 5/1455* (2013.01); *A61B 5/1495* (2013.01); *A61B 5/14551* (2013.01); *A61B 5/681* (2013.01); *A61B 5/6824* (2013.01); *G01N 21/474* (2013.01); *G01N 21/4785* (2013.01); *A61B 2560/0223* (2013.01); *A61B 2560/0233* (2013.01); *A61B 2562/0233* (2013.01); *G01J 2001/444* (2013.01); *G01N 21/31* (2013.01); *G01N 21/4795* (2013.01)

(58) Field of Classification Search
CPC ........ G01J 1/44; A61B 5/1455; A61B 5/1495; A61B 5/681
See application file for complete search history.

(56) References Cited

U.S. PATENT DOCUMENTS

| | | |
|---|---|---|
| 3,980,437 A | 9/1976 | Kishimoto et al. |
| 5,924,981 A | 7/1999 | Rothfritz et al. |
| | (Continued) | |

FOREIGN PATENT DOCUMENTS

| | | |
|---|---|---|
| EP | 2769667 A1 | 8/2014 |
| JP | 11-000323 A | 1/1999 |
| | (Continued) | |

OTHER PUBLICATIONS

Extended European Search Report for Patent Application No. EP16155870.5 dated Jul. 6, 2016 (8 pages).

*Primary Examiner* — Sang Nguyen

(74) *Attorney, Agent, or Firm* — Harness, Dickey & Pierce, P.L.C.

(57) ABSTRACT

A component measurement apparatus includes: a sensor module that receives reflected light and outputs a signal corresponding to light intensity of the reflected light; a calibration plate that outputs first reflected light to the sensor module, the first reflected light being used for comparing the light intensity of the reflected light; and a calibration unit that switches the input reflected light to the sensor module between the second reflected light reflected at a measured portion, and the first reflected light.

8 Claims, 14 Drawing Sheets

(51) Int. Cl.
  *G01N 21/47* (2006.01)
  *G01N 21/31* (2006.01)

(56) References Cited

U.S. PATENT DOCUMENTS

| | | | |
|---|---|---|---|
| 5,974,338 A | 10/1999 | Asano et al. | |
| 8,644,911 B1* | 2/2014 | Panasyuk | A61B 5/0075 600/473 |
| 9,459,038 B1* | 10/2016 | Read | F25D 21/008 |
| 2002/0198443 A1* | 12/2002 | Ting | A61B 5/021 600/323 |
| 2008/0004533 A1* | 1/2008 | Jansen | A61B 5/0059 600/476 |
| 2009/0238699 A1* | 9/2009 | Sanford | F04B 39/08 417/307 |
| 2009/0326383 A1* | 12/2009 | Barnes | A61B 5/0059 600/476 |
| 2009/0327171 A1* | 12/2009 | Tan | G06F 3/015 706/12 |
| 2010/0210924 A1* | 8/2010 | Parthasarathy | A61B 5/0002 600/301 |
| 2011/0092811 A1 | 4/2011 | Yasui | |
| 2011/0127414 A1* | 6/2011 | Engelhardt | G01N 21/278 250/252.1 |
| 2011/0140003 A1 | 6/2011 | Beck et al. | |
| 2011/0180693 A1* | 7/2011 | Ritter | G01J 1/46 250/214 A |
| 2012/0166092 A1 | 6/2012 | Maruo | |
| 2014/0240513 A1* | 8/2014 | Funamoto | G01J 3/10 348/164 |
| 2015/0009500 A1* | 1/2015 | Wong | G01R 35/005 356/402 |
| 2015/0216482 A1* | 8/2015 | Kasahara | A61B 5/1118 600/301 |

FOREIGN PATENT DOCUMENTS

| | | |
|---|---|---|
| JP | 2010-148853 A | 7/2010 |
| WO | WO-01-73405 A1 | 10/2001 |

* cited by examiner

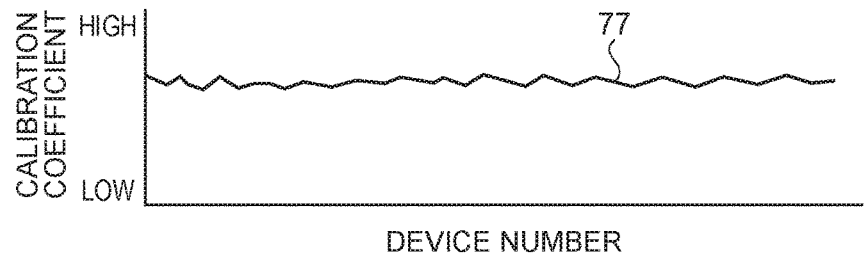
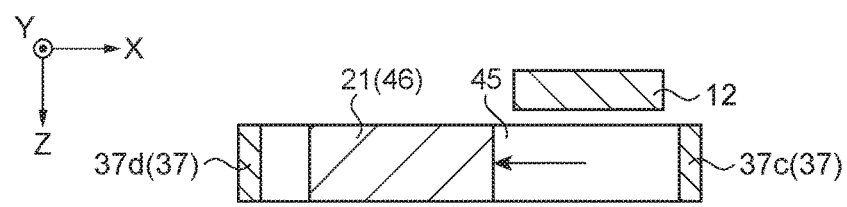
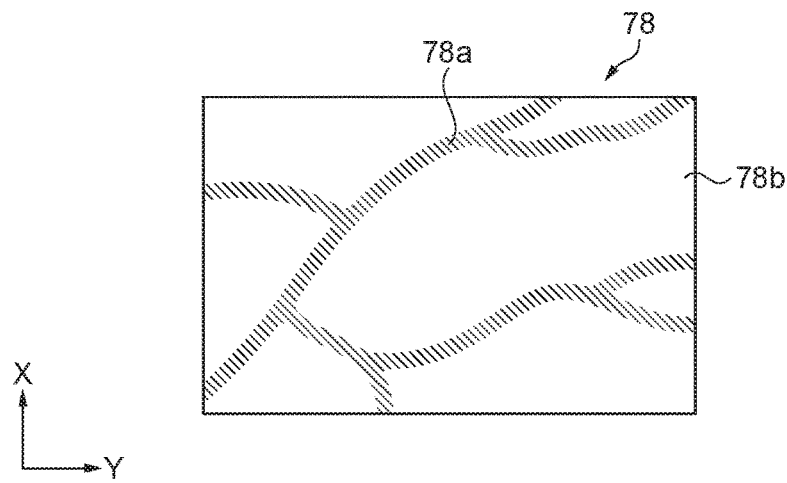
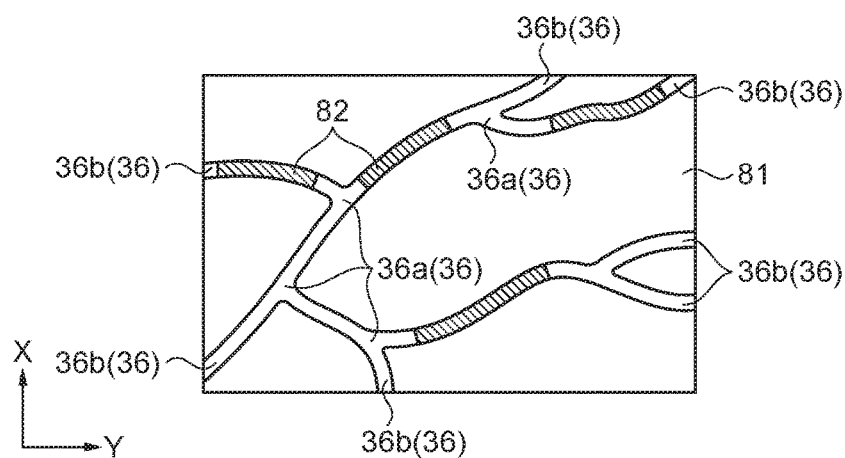

INFORMATION ACQUISITION APPARATUS AND INFORMATION ACQUISITION METHOD

BACKGROUND

1. Technical Field

The present invention relates to an information acquisition apparatus and an information acquisition method.

2. Related Art

Apparatuses that acquire biological information of a subject in a noninvasive fashion are in use. Such apparatuses put a small burden on subjects, and have high safety. One such apparatus is disclosed in JP-A-11-323 as a noninvasive blood analyzing apparatus that acquires information of blood components using light. According to this publication, a sensor is brought into contact with the subject's skin surface, and measurement light is applied into the body of the subject. Hemoglobin in the blood absorbs light of specific wavelengths. The reflected light from the subject is analyzed to detect the proportion of the oxygenated form of hemoglobin. The apparatus also detects biological information such as information of blood components.

The apparatus described in the foregoing publication detects blood information from a blood vessel selected as a test object. The apparatus emits light from a light source unit, and an imaging section receives light. The light source unit and the imaging section are electronic components, and undergo changes over time. The quantity of light from the light source decreases, and the imaging section lowers its sensitivity to light. The accuracy of the detected light information thus decreases with time. There accordingly is a need for an information acquisition apparatus that can accurately detect the characteristics of reflected light from an object even when sensor sensitivity changes with time.

SUMMARY

An advantage of some aspects of the invention is to solve the problems described above, and the invention can be implemented as the following forms or application examples.

APPLICATION EXAMPLE 1

An information acquisition apparatus according to this application example includes: a photoreceiver that receives second reflected light reflected at an object, and that outputs a signal corresponding to light intensity of the second reflected light; a calibrator having a stable reflectance that outputs first reflected light to the photoreceiver, the first reflected light being used for comparing the light intensity of the second reflected light; and a switcher that switches the input light to the photoreceiver between the second reflected light and the first reflected light.

According to this application example, the information acquisition apparatus includes the photoreceiver, the calibrator, and the switcher. The switcher switches the input light to the photoreceiver. The switcher enters either the second reflected light reflected at the object, or the first reflected light reflected at the calibrator to the photoreceiver. Upon receiving the second reflected light, the photoreceiver outputs a signal corresponding to the light intensity of the second reflected light reflected at the object. Upon reflecting light, the object absorbs light of specific wavelengths that vary with the components of the object. Information of the object can thus be acquired by analyzing the output light intensity of the second reflected light from the photoreceiver.

Upon receiving the first reflected light, the photoreceiver outputs a signal corresponding to the light intensity of the reflected light at the calibrator. The light applied to the calibrator and the object varies with time, and the rate at which the photoreceiver converts the reflected light into a signal also varies with time. The calibrator has a stable reflectance. The amount of change of the detected light intensity of the reflected light at the calibrator has a correlation with the effect of changes occurring in the light applied to the calibrator and the object, and the effect of changes occurring in the rate at which the photoreceiver converts the reflected light into a signal. The amount of change of the detected light intensity of the reflected light at the calibrator, and the detected light intensity of the reflected light at the object can thus be used to accurately detect the characteristics of the reflected light at the object.

APPLICATION EXAMPLE 2

In the information acquisition apparatus according to the application example, when entering the second reflected light to the photoreceiver, the switcher moves the calibrator to a storage position where a light path of the second reflected light is not blocked.

According to this application example, when entering the second reflected light to the photoreceiver, the switcher moves the calibrator to the storage position. The light path of the second reflected light is not blocked at the storage position. The second reflected light can thus enter the photoreceiver without being blocked by the calibrator.

APPLICATION EXAMPLE 3

In the information acquisition apparatus according to the application example, when entering the first reflected light to the photoreceiver, the switcher moves the calibrator to a block position where the light path of the second reflected light is blocked.

According to this application example, when entering the first reflected light to the photoreceiver, the switcher moves the calibrator to the block position. The block position blocks the light path of the second reflected light. The first reflected light can thus enter the photoreceiver, whereas the second reflected light is blocked from entry.

APPLICATION EXAMPLE 4

The information acquisition apparatus according to the application example includes a calibration arithmetic section that calibrates light intensity information of the second reflected light using light intensity information of the first reflected light.

According to this application example, the calibration arithmetic section calibrates the light intensity information of the second reflected light using the light intensity information of the first reflected light. The first reflected light represents the reflected light off the calibrator into the photoreceiver. The second reflected light represents the reflected light reflected at the object. The calibration arithmetic section can thus clearly distinguish the object against the calibrator. Time-dependent changes occurring in the light source irradiating the calibrator and the object, and in the photoreceiver can thus have reduced effects in analyzing the second reflected light.

APPLICATION EXAMPLE 5

In the information acquisition apparatus according to the application example, the photoreceiver includes: a light-emitting device that emits light applied to the calibrator or the object; and a light-receiving device that receives the first reflected light or the second reflected light, the light-emitting device and the light-receiving device having optical axes in the same direction.

According to this application example, the photoreceiver includes the light-emitting device and the light-receiving device. The light-emitting device and the light-receiving device have optical axes in the same direction. The light-emitting device emits light in a predetermined directional characteristic. The direction with the highest light quantity in the light of this directional characteristic is the optical axis of the light-emitting device. The light-receiving device has a predetermined directional characteristic for the sensitivity of the light it receives. The direction with the highest sensitivity in the sensitivity directional characteristic is the optical axis of the light-receiving device. In the photoreceiver, the direction with a high emission quantity and the direction with the highest photoreception sensitivity are the same.

The photoreceiver can thus receive the first reflected light with good sensitivity with the calibrator installed in the direction of the optical axes of the light-emitting device and the light-receiving device. Likewise, the photoreceiver can receive the second reflected light with good sensitivity with the object placed in the direction of the optical axes of the light-emitting device and the light-receiving device.

APPLICATION EXAMPLE 6

In the information acquisition apparatus according to the application example, the calibrator contains polytetrafluoroethylene.

According to this application example, the calibrator contains polytetrafluoroethylene. Polytetrafluoroethylene reflects near-infrared light without absorbing it. This makes it possible to efficiently obtain the first reflected light used for calibration.

APPLICATION EXAMPLE 7

The information acquisition apparatus according to the application example includes a control section that controls the switcher switching the input light to the photoreceiver between the first reflected light and the second reflected light.

According to this application example, the control section controls the switcher. The switcher switches the first reflected light and the second reflected light for entry into the photoreceiver under the control of the control section. Because the control section switches the entry of the first reflected light and the second reflected light according to the operation procedure, the procedures for the subject can be reduced.

APPLICATION EXAMPLE 8

An information acquisition method according to this application example includes: installing an information acquisition apparatus on an object; applying light to a calibrator built into the information acquisition apparatus, and detecting light intensity of first reflected light reflected at the calibrator; applying light to the object, and detecting light intensity of second reflected light reflected at the object; acquiring information of the object using the light intensity of the first reflected light and the light intensity of the second reflected light; and repeating the detection of light intensity of the first reflected light, the detection of light intensity of the second reflected light, and the acquisition of information of the object while the information acquisition apparatus is being installed on the object.

According to this application example, the information acquisition apparatus is installed on the object. Light is applied to the calibrator, and the intensity of the first reflected light reflected at the calibrator is detected. Light is applied to the object, and the intensity of the second reflected light reflected at the object is detected. Information of the object is then acquired using the light intensity of the first reflected light, and the light intensity of the second reflected light.

The light intensity detection of the first reflected light, the light intensity detection of the second reflected light, and the acquisition of the object information are repeated with the information acquisition apparatus installed on the object. Changes in object information can thus be collected even when the object is moving.

BRIEF DESCRIPTION OF THE DRAWINGS

The invention will be described with reference to the accompanying drawings, wherein like numbers reference like elements.

FIGS. 9A to 9D are schematic views explaining the biological information acquisition method.

DESCRIPTION OF EXEMPLARY EMBODIMENTS

Figure 1A:
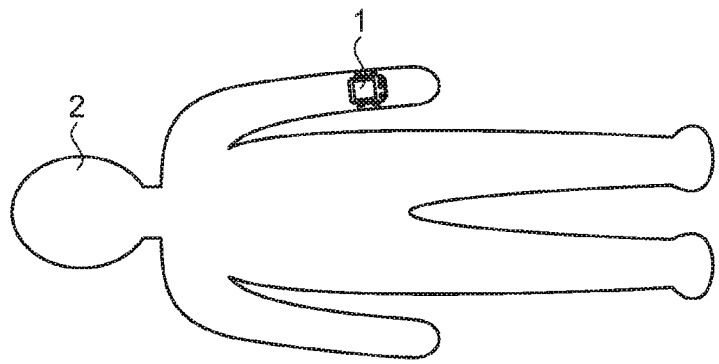
FIG. 1A is a schematic view explaining an installation example of a component measurement apparatus according to First Embodiment.

Embodiments are described below with reference to the accompanying drawings.

Note that the members in the drawings are shown in sizes that make the members recognizable in the drawings, and are not to scale relative to actual size or each other.

First Embodiment

The present embodiment describes typical examples of a component measurement apparatus, and a component information acquisition method that analyzes blood components using the component measurement apparatus, with reference to the accompanying drawings.

A component measurement apparatus according to First Embodiment is described with reference to FIG. 1A to FIG. 5. FIG. 1A is a schematic view explaining an installation example of the component measurement apparatus. As illustrated in FIG. 1A, the component measurement apparatus 1 as an information acquisition apparatus is installed on a wrist of a subject 2. The component measurement apparatus 1 is a medical device for measuring blood components of the subject 2 in a noninvasive fashion, and represents medical equipment. The component measurement apparatus 1 measures components of the blood flowing in the blood vessels in the wrist. In the present embodiment, for example, the blood component measured is glucose concentration. Glucose concentration measurement enables measuring glucose levels.

Figure 1B:
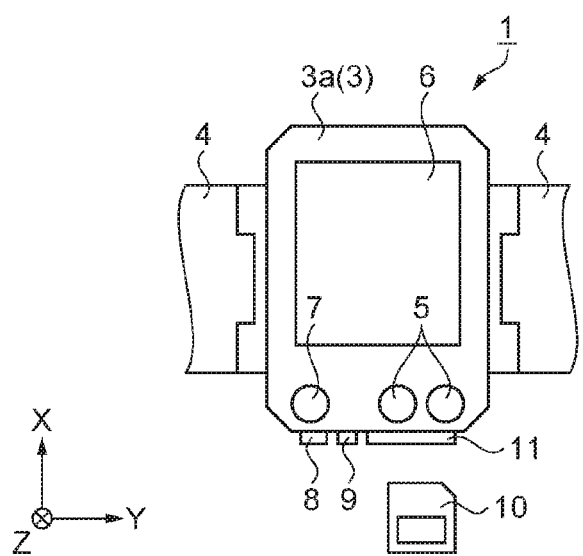
FIGS. 1B and 1C are schematic plan views representing the structure of the component measurement apparatus.
Figure 1C:
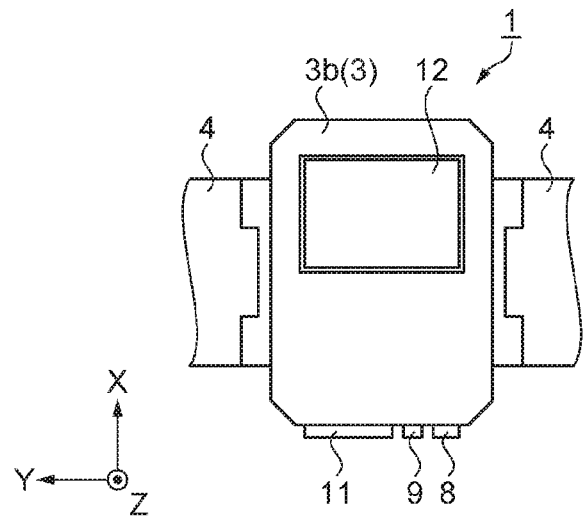

FIGS. 1B and 1C are schematic plan views representing the structure of the component measurement apparatus. FIG. 1B shows the top surface of the component measurement apparatus 1. FIG. 1C shows the back surface of the component measurement apparatus 1. As illustrated in FIG. 1B, the component measurement apparatus 1 has a shape similar to the shape of a wrist watch. The component measurement apparatus 1 has a main body case 3. The main body case 3 has a fixing band 4 on both sides (left and right in the figure). The fixing band 4 is used to fix the component measurement apparatus 1 to a measured portion such as the wrist and arm of the subject 2. The fixing band 4 uses a Magic Tape®. In referring to the component measurement apparatus 1, Y direction is the direction of extension of the fixing band 4, and X direction in the direction of extension of the arm of the subject 2. The direction in which the component measurement apparatus 1 faces the subject 2 is Z direction. X-, Y-, and Z-directions are orthogonal to each other.

The main body case 3 has a surface 3a that faces outward upon mounting the component measurement apparatus 1 on the subject 2. On the surface 3a of the main body case 3 are installed operation switches 5, a touch panel 6, and a speaker 7. The subject 2 enters measurement start instructions through the operation switches 5 and the touch panel 6. The touch panel 6 displays measurement result data. The component measurement apparatus 1 through the speaker 7 produces a warning sound to caution the subject 2.

A communication section 8 for communicating with external devices is installed on a side surface of the main body case 3. The communication section 8 may be a section that communicates via a cable, or a wireless communication module that performs wireless communications. A connector 9 used to charge a rechargeable battery (not illustrated) is also installed. There is also installed a reader/writer 11 for installing a memory card 10. The memory card 10 is rewritable nonvolatile memory, such as flash memory, ferroelectric memory, and magnetoresistive memory.

As shown in FIG. 1C, a sensor module 12 is installed as a photoreceiver on the back surface 3b side of the main body case 3. When in use, the sensor module 12 is brought close to the skin of the subject 2. The sensor module 12 applies measurement light to the skin of the subject 2, and receives reflected light. The sensor module 12 is a thin image sensor with a built-in light source and photosensor array.

Figure 2:
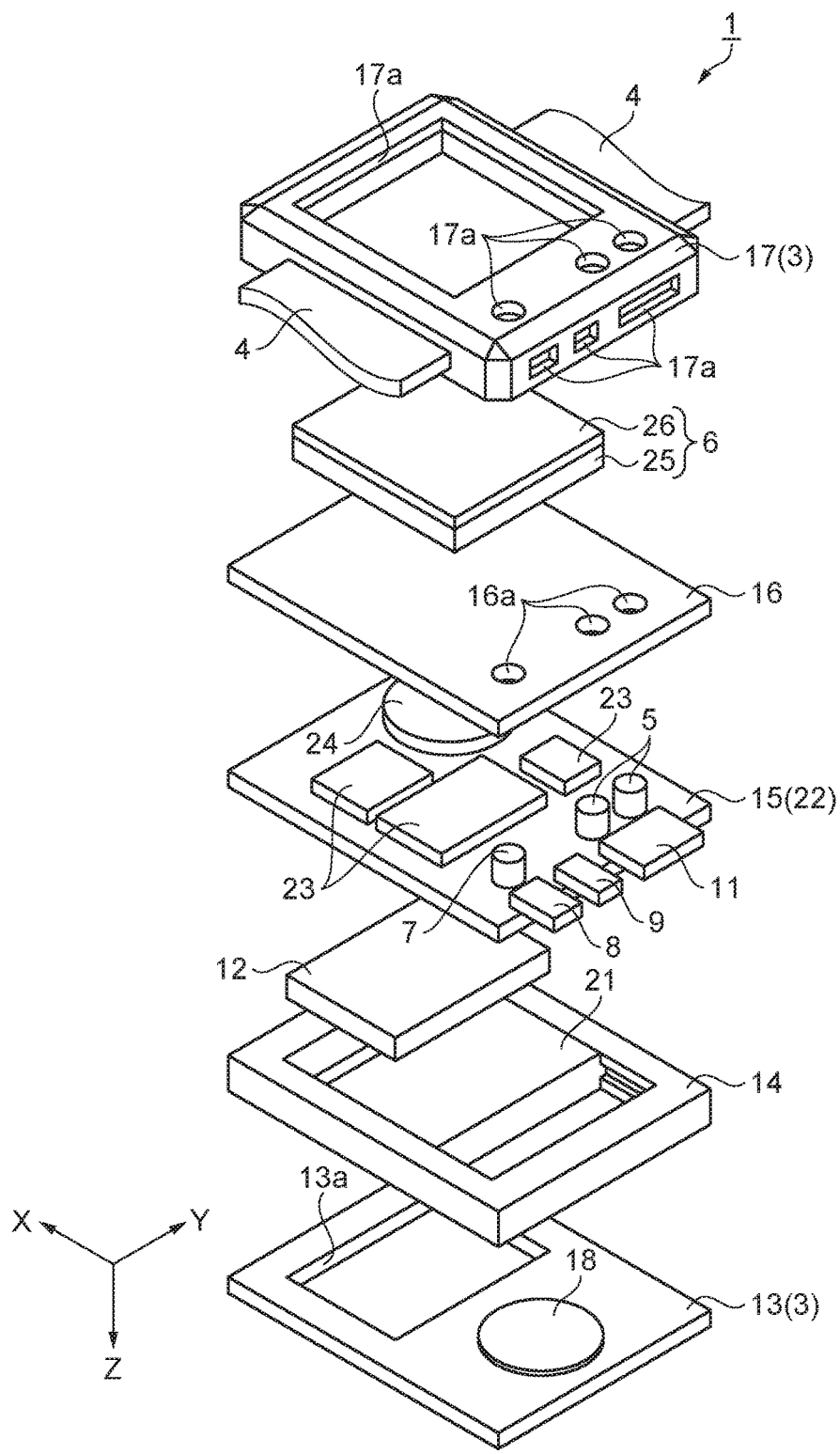
FIG. 2 is an exploded perspective view representing the structure of the component measurement apparatus.

FIG. 2 is an exploded perspective view illustrating the structure of the component measurement apparatus. As illustrated in FIG. 2, the component measurement apparatus 1 is configured from a caseback 13, a calibration unit 14 (switcher), the sensor module 12, a circuit unit 15, a spacer 16, the touch panel 6, and a top case 17, which are stacked in this order in Z direction. The caseback 13 and the top case 17 constitute the main body case 3.

The caseback 13 is a plate-shaped member that comes into contact with the subject 2. The caseback 13 has a quadrangular window portion 13a installed on X direction side. The window portion 13a is provided at a location facing the sensor module 12. The sensor module 12 can be seen through the window portion 13a when viewed into Z direction. A light transmissive plate such as glass may be disposed in the window portion 13a. This makes it possible to prevent entry of dust into the main body case 3 through the window portion 13a. Such a plate also can prevent contamination of the sensor module 12.

A vibrator 18 is installed on −X direction side of the caseback 13. The vibrator 18 is adapted to vibrate the caseback 13. The component measurement apparatus 1 can function to caution the subject 2 with the vibration of the caseback 13. The member used to constitute the vibrator 18 is not particularly limited, as long as it can vibrate the caseback 13. In the present embodiment, for example, the vibrator 18 is a piezoelectric element.

A calibration plate 21 is installed as a calibrator in the calibration unit 14. The calibration plate 21 is movable along X direction. The calibration plate 21 is a plate with a reflectance that remains stable over extended time periods, and is used to detect changes occurring in the sensor module over time. The sensor module 12 is a sensor with light-emitting devices, light-receiving devices, and spectral devices installed in a grid. The sensor module 12 applies light to the subject 2, and detects the intensity of reflected light of specific wavelengths.

The circuit unit 15 has a circuit board 22. On the circuit board 22 is installed an electrical circuit 23 that drives and controls the vibrator 18, the calibration unit 14, the sensor module 12, and the touch panel 6. The electrical circuit 23 is configured from a plurality of semiconductor chips. The operation switches 5, the speaker 7, the communication section 8, the connector 9, the reader/writer 11, and a rechargeable battery 24 are also installed on the circuit board 22. The rechargeable battery 24 is electrically connected to the connector 9, and is chargeable via the connector 9.

The spacer 16 is a structure installed between the circuit unit 15 and the touch panel 6. With the plurality of devices installed on the surface of the circuit unit 15 on −Z direction side, the circuit unit 15 has irregularities on this surface. The spacer 16 is installed over the circuit board 22, and serves to provide a flat surface against the touch panel 6. The spacer 16 has a plurality of holes 16a, and the operation switches 5 and the speaker 7 penetrate through the holes 16a.

The touch panel 6 is structured to include a display section 25, and an operation input section 26 installed on the display section 25. The display section 25 is not particularly limited, as long as it can display electronic data in the form of an image. The display section 25 may be, for example, a liquid crystal display device, or an OLED (organic light-emitting diode) display device. In the present embodiment, the display section 25 uses, for example, OLED.

The operation input section 26 is an input section with transparent electrodes disposed in a grid on a surface of a transparent plate. Upon an operator touching the transparent electrodes, current passes across the crossing electrodes, and enables detection of the location touched by the operator. The transparent plate may be a resin sheet or a glass plate, as long as it is light transmissive. The transparent electrodes may be, for example, IGO (indium-gallium oxide), ITO (indium Tin Oxide), or ICO (indium-cerium oxide), as long as it is a light-transmissive conductive film. The display section 25 displays information such as a measurement status, and measurement results. The operation switches 5 are switches used to operate the component measurement apparatus 1, as is the operation input section 26. An operator operates the operation input section 26 and the operation switches 5 to enter various instructions, such as an instruction for starting a measurement of glucose level, and measurement conditions.

The top case 17 has a plurality of holes 17a. The operation input section 26, the operation switches 5, the speaker 7, the communication section 8, the connector 9, and the reader/writer 11 are exposed through the holes 17a. The components from the calibration unit 14 to the touch panel 6 are housed between the caseback 13 and the top case 17.

Figure 3A:
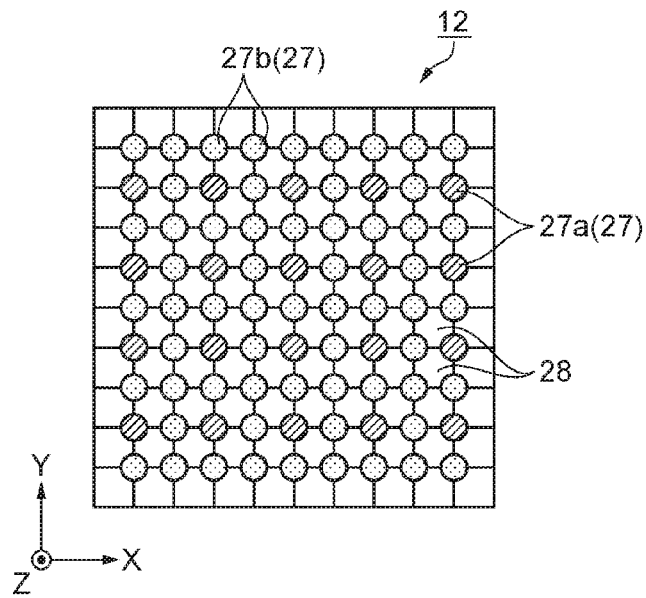
FIG. 3A is a schematic plan view representing the structure of a sensor module.
Figure 3B:
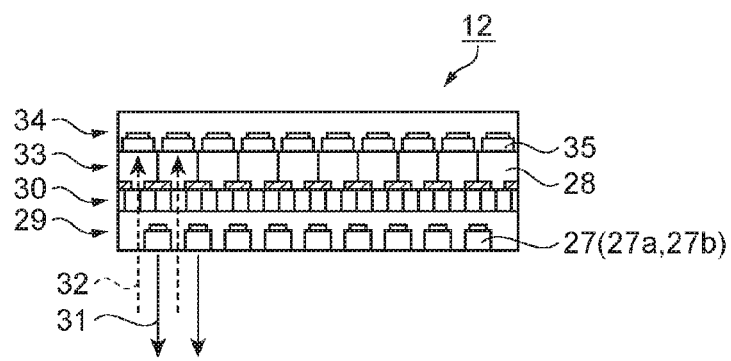
FIG. 3B is a schematic side sectional view representing the structure of the sensor module.
Figure 3C:
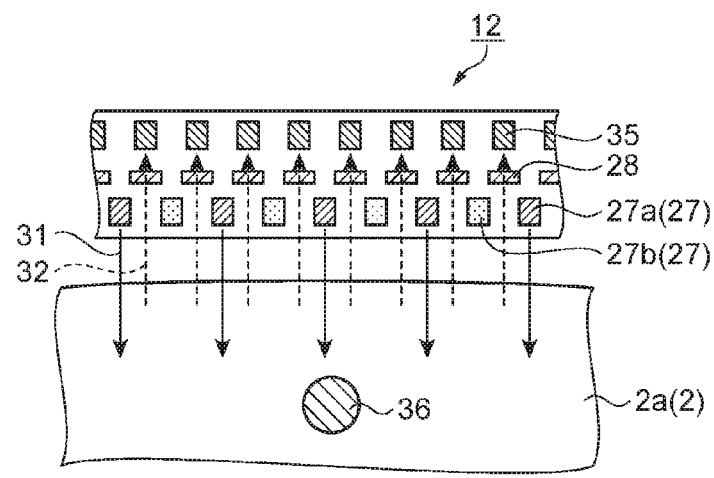
FIG. 3C is a partial schematic side sectional view explaining an operation of the sensor module.

FIG. 3A is a schematic plan view showing the structure of the sensor module 12, as viewed from the back surface 3b side. FIG. 3B is a schematic side sectional view illustrating the structure of the sensor module. FIG. 3C is a partial schematic side sectional view explaining the operation of the sensor module. As illustrated in FIG. 3A, the sensor module 12 has a two-dimensional array of light-emitting devices 27 in a grid. Between the adjacent light-emitting devices 27 are installed spectral devices 28.

The arrayed directions of the light-emitting devices 27 and the spectral devices 28 are X and Y directions. The light-emitting devices 27 and the spectral devices 28 are disposed at the same intervals in X and Y directions. The light-emitting devices 27 and the spectral devices 28 are disposed in a staggered fashion in X and Y directions with a predetermined distance in between. Accordingly, the spectral devices 28 have wide non-overlapping portions with the light-emitting devices 27 as viewed from the back surface 3b side. This structure permits light propagating from the subject 2 side to reach the spectral devices 28.

The light-emitting devices 27 are configured from imaging light-emitting devices 27a and measurement light-emitting devices 27b. In the figure, the 1st, 3rd, 5th, 7th, and 9th rows are configured from the measurement light-emitting devices 27b. The imaging light-emitting devices 27a and the measurement light-emitting devices 27b are alternately disposed in the 2nd, 4th, 6th, and 8th rows in the figure. Four light-emitting devices 27 are installed per spectral device 28. A unit of four light-emitting devices 27 includes one imaging light-emitting device 27a, and three measurement light-emitting devices 27b.

In capturing an image to detect locations of blood vessels, the imaging light-emitting devices 27a apply light to the subject 2. The light applied by the imaging light-emitting devices 27a has a 700 nm to 900 nm wavelength range centered at 800 nm. Hemoglobin in the blood has high absorption of light at 800 nm wavelength. An image of blood vessel locations can thus be captured with light applied to the subject 2 by the imaging light-emitting devices 27a.

In capturing an image to detect blood glucose concentration, the measurement light-emitting devices 27b apply light to the subject 2. The light applied by the measurement light-emitting devices 27b has a 900 nm to 2000 nm wavelength range centered at 1450 nm. Glucose in the blood has high absorption of light at 1200 nm, 1600 nm, and 2000 nm wavelengths. Blood glucose concentration can thus be detected with light applied to the subject 2 by the measurement light-emitting devices 27b. Glucose is also called grape sugar.

For simplicity, the light-emitting devices 27 are shown as an array of 9 rows and 9 columns. The number of rows and the number of columns in the array of the light-emitting devices 27 and the spectral devices 28 are not particularly limited, and may be appropriately set. For example, the interval between these devices is preferably 1 to 1500 μm. Considering the balance between manufacturing cost and measurement accuracy, the interval is more preferably, for example, about 100 to 1500 μm. The light-emitting devices 27 and the spectral devices 28 are not limited to the layered configuration, and these may be disposed side by side on a plane. In the present embodiment, for example, 250 rows× 250 columns of light-emitting devices 27 are installed. The interval between the light-emitting devices 27 is not particularly limited either. In the present embodiment, for example, the interval between the light-emitting devices 27 is 0.1 mm. The sensor module 12 can thus also function as an imaging device.

As illustrated in FIG. 3B, the array of light-emitting devices 27 constitutes a light-emitting layer 29 (light source). The light-emitting devices 27 represent an irradiator that applies measurement light. The light-emitting devices 27 are not particularly limited, as long as it can emit near-infrared rays that can pass through the subcutaneous tissue. The light-emitting devices 27 may use, for example, LED (light emitting diode), or OLED (organic light-emitting diode).

A light-shielding layer 30 is installed over the light-emitting layer 29. The measurement light 31 emitted by the light-emitting layer 29 toward the subject 2 is reflected at the subcutaneous tissue of the subject 2, and becomes reflected light 32. The light-shielding layer 30 passes light directed to the spectral devices 28, but selectively blocks other light. A spectral layer 33 is installed over the light-shielding layer 30. The spectral devices 28 are arrayed in a grid in the spectral layer 33. The spectral devices 28, also called etalons, are devices that selectively pass near-infrared rays of predetermined wavelengths. The spectral devices 28 in response to an input instruction signal pass reflected light 32 of the wavelength specified by the instruction signal. The spectral devices 28 include a pair of oppositely disposed mirrors, and an electrostatic actuator is installed that adjusts the distance between the mirrors. The passage of reflected light 32 of predetermined wavelengths is permitted by the electrostatic actuator adjusting the distance between the mirrors.

Glucose has peak wavelengths of 1200 nm, 1600 nm, and 2000 nm. Blood sugar level can be measured by detecting transmittance at these three wavelengths. The wavelengths of the reflected light 32 passed by the spectral devices 28 are not particularly limited. In the present embodiment, the spectral devices 28, for glucose detection, pass light of, for example, 1500 nm to 1700 nm wavelengths centered at 1600 nm.

A light-receiving layer 34 is installed over the spectral layer 33. The light-receiving layer 34 has a planar two-dimensional array of light-receiving devices 35. The light-receiving devices 35 are arrayed in the same pattern as the spectral devices 28. The light-receiving devices 35 overlie the spectral devices 28 as viewed in the direction of travel of the reflected light 32.

The light-receiving devices 35 represent a photoreceiver that outputs electrical signals according to the quantity of the reflected light 32 it receives. The light-receiving devices 35 may use, for example, imaging devices such as CCD (Charge Coupled Device Image Sensor), and CMOS (Complementary Metal Oxide Semiconductor Image Sensor), as long as light intensity can be converted into electrical signals. The light-receiving devices 35 each may have a configuration that includes a plurality of devices for receiving wavelength components necessary for calibration. The sensor module 12 has its front surface on the side of the light-emitting layer 29, and is installed on the back surface 3b of the main body case 3 in such an orientation that the front surface side faces the skin surface of the subject 2.

The light-emitting devices 27 and the light-receiving devices 35 have optical axes in the same direction. The light-emitting devices 27 emit the measurement light 31 in a predetermined directional characteristic. The direction with the highest light quantity in the directional characteristic of the measurement light 31 represents the optical axis of the light-emitting device. The detection sensitivity of the light-receiving devices 35 for the reflected light 32 has a predetermined directional characteristic. The direction with the highest sensitivity in the sensitivity directional characteristic represents the optical axis of the light-receiving device 35. In the sensor module 12, the direction with a high emission quantity and the direction with the highest photoreception sensitivity are the same.

Accordingly, the sensor module 12 can receive first reflected light 32a with good sensitivity with the calibration plate 21 placed on the optical axes of the light-emitting devices 27 and the light-receiving devices 35. Likewise, the sensor module 12 can receive second reflected light 32b with good sensitivity with the measured portion 2a (object) placed on the optical axes of the light-emitting devices 27 and the light-receiving devices 35.

As illustrated in FIG. 3C, all the imaging light-emitting devices 27a in the sensor module 12 simultaneously emit light in capturing the location of a blood vessel 36. The location opposite the sensor module 12 represents the measured portion 2a. The measurement light 31 is applied over the whole region of the measured portion 2a of the subject 2. The reflected light 32 is received by all the light-receiving devices 35, and a biological image is acquired. For the measurement of blood components, only the specified devices in the measurement light-emitting devices 27b emit light, and the reflected light 32 is received by the specified devices in the light-receiving devices 35.

Figure 4A:
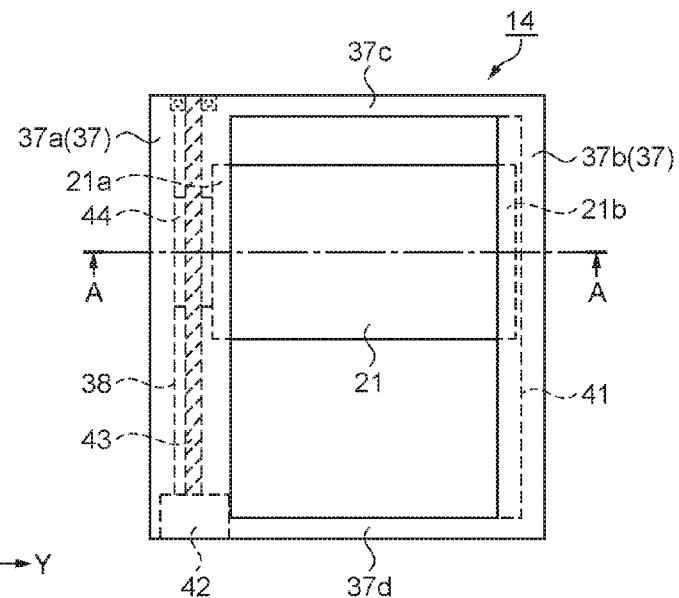
FIG. 4A is a schematic plan view representing the structure of a calibration unit.
Figure 4B:
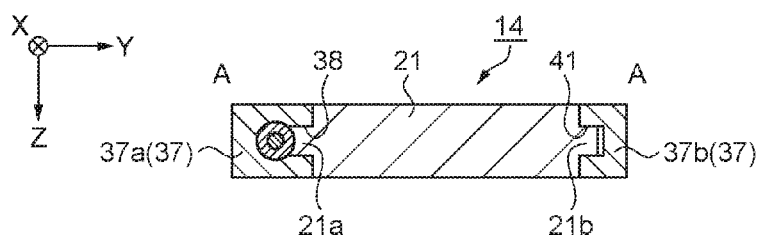
FIG. 4B is a schematic side sectional view representing the structure of the calibration unit.
Figure 4C:
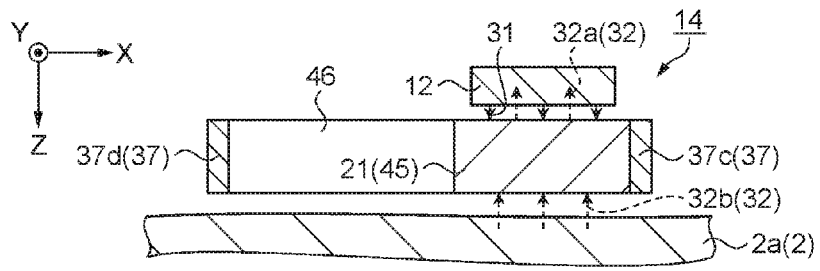
FIGS. 4C and 4D are schematic views explaining an operation of the calibration unit.
Figure 4D:
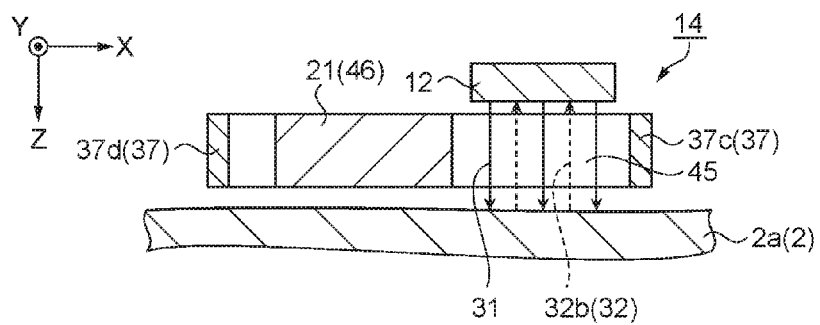

FIG. 4A is a schematic plan view representing the structure of the calibration unit. FIG. 4B is a schematic side sectional view representing the structure of the calibration unit, taken at line A-A of FIG. 4A. FIGS. 4C and 4D are schematic views explaining the operation of the calibration unit. As illustrated in FIGS. 4A and 4B, the calibration unit 14 has a quadrangular frame 37. The frame 37 has a first guide member 37a and a second guide member 37b located on −Y direction side and +Y direction side, respectively. The first guide member 37a and the second guide member 37b are disposed parallel to each other, and extend in X direction. The first guide member 37a and the second guide member 37b are joined to each other with a first support member 37c and a second support member 37d.

The calibration plate 21 is installed inside the frame 37. A first guide groove 38, extending in X direction, is installed in the first guide member 37a. Similarly, a second guide groove 41, extending in X direction, is installed in the second guide member 37b. The calibration plate 21 has a first raised portion 21a on the surface on the side of −Y direction, and a second raised portion 21b on the surface on the side of +Y direction. The first raised portion 21a is inserted in the first guide groove 38, and slides along the first guide groove 38 in X direction. The second raised portion 21b is inserted in the second guide groove 41, and slides along the second guide groove 41 in X direction. The calibration plate 21 is thus movable in X direction.

A motor 42 is installed on −X direction side of the first guide member 37a, and a threaded rod 43 is installed on the rotational axis of the motor 42. A nut 44 is installed at the end of the first raised portion 21a on −Y direction side, and the threaded rod 43 is threaded into the nut 44. The nut 44 thus moves in X direction with the rotation of the threaded rod 43 as the motor 42 rotates the threaded rod 43. Because the nut 44 is fixed to the calibration plate 21, the calibration plate 21 can be moved back and forth in X direction by driving the motor 42.

As illustrated in FIG. 4C, the sensor module 12 is located on −Z direction side of the frame 37. The sensor module 12 is located on +X direction side. The +X direction side and the −X direction side inside the frame 37 are a block position 45 and a storage position 46, respectively. With the calibration plate 21 located at the block position 45, the reflected light 32 at the subject 2 represents the second reflected light 32b. Upon being moved to the block position 45 by the calibration unit 14, the calibration plate 21 blocks the light path of the second reflected light 32b. By being blocked, the second reflected light 32b does not reach the sensor module 12. With the sensor module 12 applying the measurement light 31 to the calibration plate 21, the reflected light 32 at the calibration plate 21 represents the first reflected light 32a. The first reflected light 32a enters the sensor module 12.

The material of the calibration plate 21 is not particularly limited, as long as it can stably reflect infrared light over extended time periods. Materials such as polytetrafluoroethylene, and metals may be used. Polytetrafluoroethylene is also called Teflon®. In the present embodiment, for example, the calibration plate 21 is a plate produced by compacting and sintering polytetrafluoroethylene particles. The plate has a high reflectance of about 98% or more in a 1500 nm to 1700 nm wavelength region.

As illustrated in FIG. 4D, the calibration unit 14 moves the calibration plate 21 to the storage position 46 under the drive of the motor 42. This leaves a space in the block position 45, allowing the measurement light 31 and the reflected light 32 to pass through the calibration unit 14. The sensor module 12 applies the measurement light 31 to the measured portion 2a, and receives the second reflected light 32b reflected at the measured portion 2a. The sensor module 12 can capture the measured portion 2a, and detect the second reflected light 32b in the manner described above.

Figure 5:
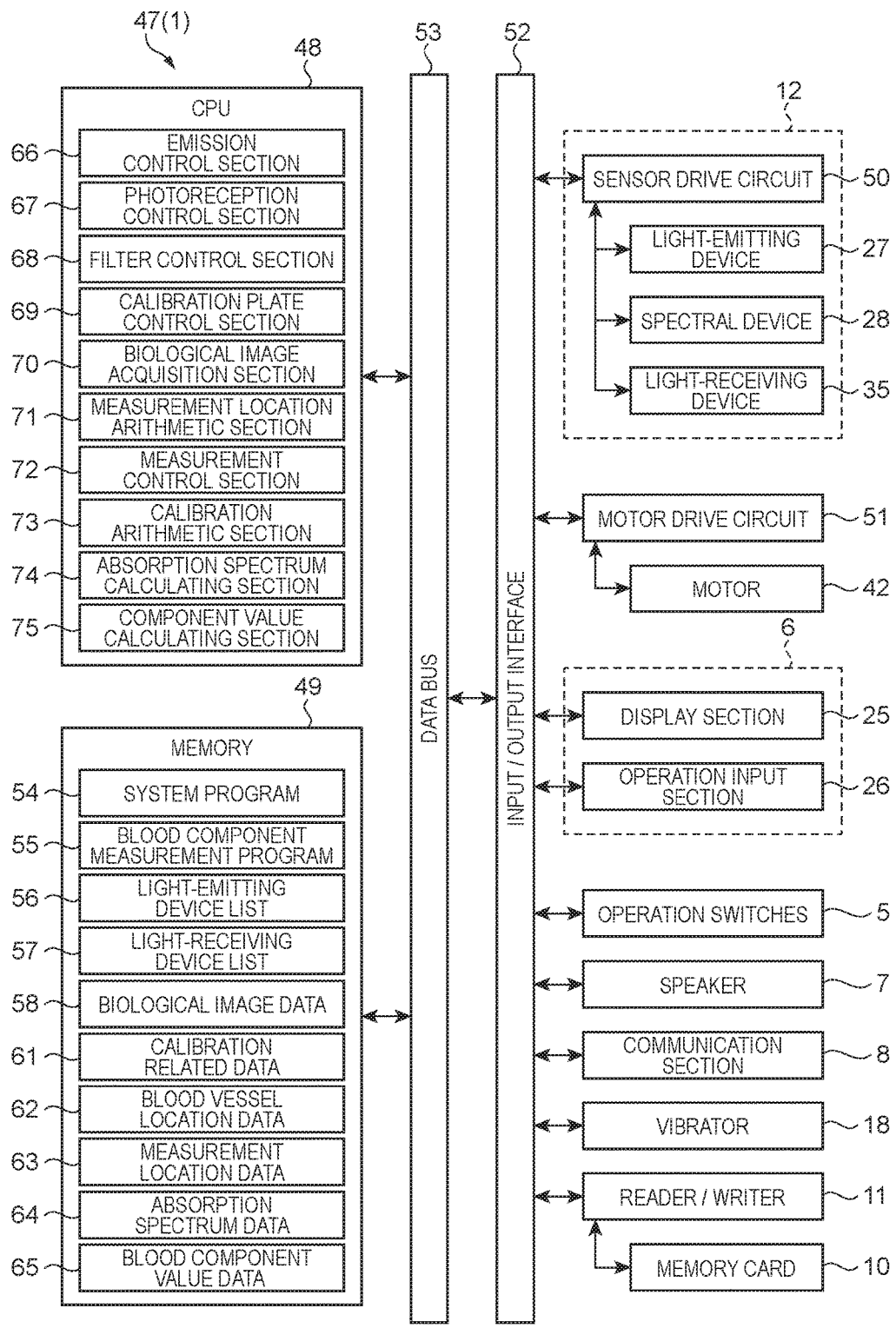
FIG. 5 is a block diagram representing the electrical control of the component measurement apparatus.

FIG. 5 is a block diagram representing the electrical control of the component measurement apparatus. Referring to FIG. 5, the component measurement apparatus 1 includes a controller 47 that controls the operation of the component measurement apparatus 1. The controller 47 includes a CPU 48 (Central Processing Unit) as a processor that performs various arithmetic processes, and memory 49 that stores a variety of information. A sensor drive circuit 50, a motor drive circuit 51, the operation input section 26, the display section 25, the operation switches 5, the speaker 7, the vibrator 18, the communication section 8, and the reader/writer 11 are connected to the CPU 48 via an input/output interface 52 and a data bus 53.

The sensor drive circuit 50 is a circuit that drives the sensor module 12. The sensor drive circuit 50 drives the light-emitting devices 27, the spectral devices 28, and the light-receiving devices 35 constituting the sensor module 12. The light-emitting devices 27, the spectral devices 28, and the light-receiving devices 35 are two-dimensionally arrayed in a planar fashion in the sensor module 12. The sensor drive circuit 50 turns on and off the light-emitting devices 27 according to instruction signals from the CPU 48. The sensor drive circuit 50 sets a wavelength for passage of reflected light 32 through the spectral devices 28, using an instruction signal from the CPU 48. The sensor drive circuit 50 amplifies the light intensity signal of the light received by the light-receiving devices 35, and sends the signal to the CPU 48 after converting it into a digital signal.

The motor drive circuit 51 is a circuit that drives the motor 42. The motor drive circuit 51 rotates the motor at the predetermined rotation speed according to instructions from the CPU 48. The motor drive circuit 51 is a circuit that moves the calibration plate 21 between the block position 45 and the storage position 46.

The display section 25 displays predetermined information according to instructions from the CPU 48. An operator operates the operation input section 26 according to the displayed content, and enters instruction content. The instruction content is sent to the CPU 48.

The speaker 7 is an audio output unit, and makes various audio outputs according to instructions from the CPU 48. The speaker 7 outputs notification sounds indicative of information such as the start and the end of a glucose level measurement, and occurrence of an error. The communication section 8 is configured from circuits such as a wireless communication circuit, a wired communication circuit, and a communication control circuit. The communication section 8 performs communications with external devices.

The vibrator 18 is a device that vibrates the caseback 13. Because the caseback 13 is in contact with the subject 2, the component measurement apparatus 1 can caution the subject 2 by vibrating the caseback 13. The subject 2 can be cautioned using the vibrator 18 when the use environment of the component measurement apparatus 1 does not permit making sound from the speaker 7.

The memory 49 is a concept that includes semiconductor memories such as RAM and ROM, and external memory devices such as a hard disc, and a DVD-ROM. Functionally, the memory 49 has a storage region set therein to store a system program 54 that describes control procedures for the operation of the component measurement apparatus 1, and a storage region set therein to store a blood component measurement program 55 that describes arithmetic procedures for estimating blood components. The memory 49 also has a storage region set therein to store a light-emitting device list 56 that represents data indicative of the locations of the light-emitting devices 27.

The memory 49 also has a storage region set therein to store a light-receiving device list 57 that represents data indicative of the locations of the light-receiving devices 35. The memory 49 also has a storage region set therein to store biological image data 58 obtained by capturing the location of the blood vessel 36 under the light emitted by all the light-emitting devices 27. The memory 49 also has a storage region set therein to store calibration related data 61 used to calibrate light intensity with the calibration unit 14. The memory 49 also has a storage region set therein to store blood vessel location data 62 indicative of the location of the blood vessel 36 computed from the biological image data 58. The memory 49 also has a storage region set therein to store measurement location data 63 indicative of the location of the blood vessel 36 being measured.

The memory 49 also has a storage region set therein to store absorption spectrum data 64 that represents the optical transmittance of the measured blood. The memory 49 also has a storage region set therein to store blood component value data 65 indicative of the blood concentrations of the measured blood components. The memory 49 also has various other storage regions set therein to serve different purposes, including a storage region that serves as a work area for the CPU 48, and a storage region that serves as temporary files.

The CPU 48 controls the measurement of blood glucose concentration according to the system program 54 and the blood component measurement program 55 stored in the memory 49. Specifically, the CPU 48 has an emission control section 66 to realize its functions. The emission control section 66 controls the switching that selectively turns on and off the light-emitting devices 27. The CPU 48 also has a photoreception control section 67. The photoreception control section 67 controls the acquisition of digital data of the light quantity received by the light-receiving devices 35. The CPU 48 also has a filter control section 68. The filter control section 68 controls the sensor drive circuit 50 to switch the wavelength that can pass through the spectral devices 28. The CPU 48 also has a calibration plate control section 69 as a control section. The calibration plate control section 69 controls the motor drive circuit 51 to drive the motor 42, and switch the position of the calibration plate 21. This allows the entry of reflected light to the sensor module 12 to be switched between the first reflected light 32a and the second reflected light 32b depending on the situation, without being operated by the subject 2.

The CPU 48 also has a biological image acquisition section 70. The biological image acquisition section 70 acquires a biological image of a portion of body directly below the sensor module 12. The acquisition of a biological image is made possible by the appropriate use of biological image capturing techniques, such as a known vein authentication technique. Specifically, all the light-receiving devices 35 are used to capture an image under the light emitted by all the imaging light-emitting devices 27a of the sensor module 12. The captured image generates a biological image. The biological image acquired by the biological image acquisition section 70 is stored as the biological image data 58 in the memory 49.

The CPU 48 also has a measurement location arithmetic section 71. The measurement location arithmetic section 71 performs a predetermined image process on the biological image, and acquires blood vessel location data. Specifically, a vein pattern is identified from the biological image using a known technique. For example, the biological image is subjected to pixel-wise binarization or filtering relative to a reference luminance. In the processed biological image, pixels with luminance values below the reference luminance indicate blood vessels, and pixels with luminance values equal to or greater than the reference luminance indicate a non-blood vessel region. The blood vessel location data acquired by the measurement location arithmetic section 71 is stored as blood vessel location data 62 in the memory 49.

The measurement location arithmetic section 71 selects a measurement target by selecting a location of blood vessel 36 satisfying predetermined selection conditions. The location selected as the measurement target may be a single blood vessel 36, or more than one blood vessel 36. The data of the blood vessel 36 at the selected measurement target location is stored as the measurement location data 63 in the memory 49.

The measurement location arithmetic section 71 selects a measurement light-emitting device 27b and a light-receiving device 35 that are to be driven for the blood vessel 36 at each measurement location. Specifically, the measurement location arithmetic section 71 selects a light-emitting device 27 and a light-receiving device 35 that lie on a straight line orthogonal to the center line of the blood vessel 36 at the measurement location. Here, the measurement light-emitting device 27b and the light-receiving device 35 are selected in such a manner that the distance between the measurement location and the light-emitting device 27, and the distance between the measurement location and the light-receiving device 35 take values close to the optimum distance. The measurement light-emitting device 27b so selected is stored as the light-emitting device list 56 in the memory 49. The light-receiving device 35 so selected is stored as the light-receiving device list 57 in the memory 49.

The CPU 48 also has a measurement control section 72. The measurement control section 72 makes the sensor drive circuit 50 turn on the measurement light-emitting device 27b. The measurement control section 72 causes the sensor drive circuit 50 to drive the light-receiving device 35 for detection of the light intensity of the reflected light 32. Here, the light intensity is the light intensity of the light that has passed through the blood vessel 36. The CPU 48 also has a calibration arithmetic section 73. The calibration arithmetic section 73 applies the measurement light 31 to the calibration plate 21, and enters the reflected light 32 to the light-receiving device 35. The calibration arithmetic section 73 measures the detection sensitivity of the sensor module 12, and computes a calibration coefficient. With the calibration coefficient, the measurement control section 72 calibrates the measured light intensity.

The CPU 48 also has an absorption spectrum calculating section 74. The absorption spectrum calculating section 74 generates an absorption spectrum of the measured blood vessel 36. Specifically, the absorption spectrum calculating section 74 calculates the transmittance T of the blood vessel 36 using the light intensity of the light received by the light-receiving device 35, and generates an absorption spectrum. The absorption spectrum so calculated is stored as the absorption spectrum data 64 in the memory 49. The measurement may be made at one or more wavelengths λ. The wavelength λ varies with the measured blood component.

The CPU 48 also has a component value calculating section 75. The component value calculating section 75 calculates a glucose concentration using the absorption spectrum. The calculation of absorption spectrum may use analysis techniques such as multiple linear regression analysis, main component regression analysis, PLS regression analysis, and independent component analysis. When there is more than one blood vessel 36 at the measurement location, a glucose concentration is calculated from the average absorption spectrum of different blood vessels 36. The calculated value is stored as the blood component value data 65 in the memory 49.

The present embodiment has been described through the case where the functions are achieved by program software using the CPU 48. However, these functions may be achieved with the use of an electronic circuit, when an electronic circuit (hardware) alone is sufficient to achieve the foregoing functions without using the CPU 48.

Figure 6A:
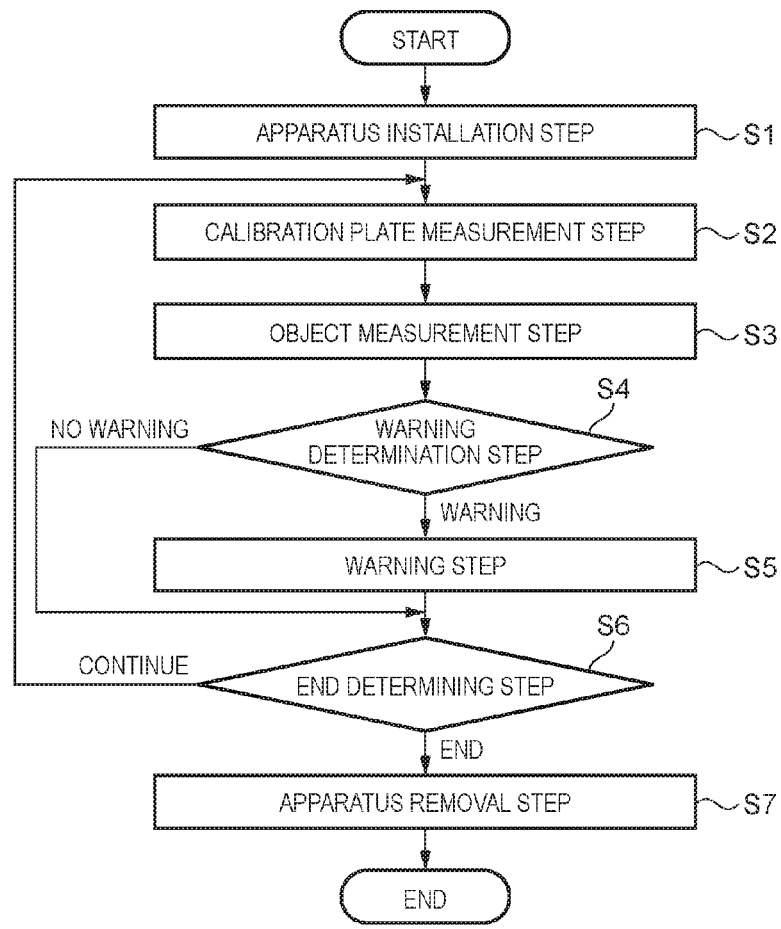
FIG. 6A is a flowchart of an information acquisition method.

The following describes an information acquisition method that uses the component measurement apparatus 1 described above, with reference to FIG. 6A to FIG. 11D. FIG. 6A is a flowchart representing the information acquisition method.

In the flowchart of FIG. 6A, step S1 corresponds to an apparatus installation step, in which an operator installs the component measurement apparatus 1 on the subject 2. The sequence then goes to step S2. Step S2 corresponds to a calibration plate measurement step. The measurement light 31 is applied to the calibration plate 21, and the light-receiving device 35 detects the reflected light 32. In this step, the calibration arithmetic section 73 calculates the calibration coefficient. Step S3 is an object measurement step. In this step, the measurement light 31 is applied to the measured portion 2a, and the light-receiving device 35 detects the reflected light 32. Blood glucose is measured in this step. The sequence then goes to step S4. Step S4 is a warning determination step, which determines whether to warn the subject 2. When warning the subject 2, the sequence goes to step S5. The sequence goes to step S6 when not warning the subject 2.

Step S5 is a warning step. This step warns the subject 2 that an abnormal event has occurred. The sequence then goes to step S6. Step S6 is an end determining step, which determines whether to continue or end the measurement. When continuing the measurement, the sequence goes to step S2. The sequence goes to step S7 when ending the measurement. Step S7 is an apparatus removal step. This step removes the component measurement apparatus 1 from the subject 2. This completes the information acquisition process.

Figure 6B:
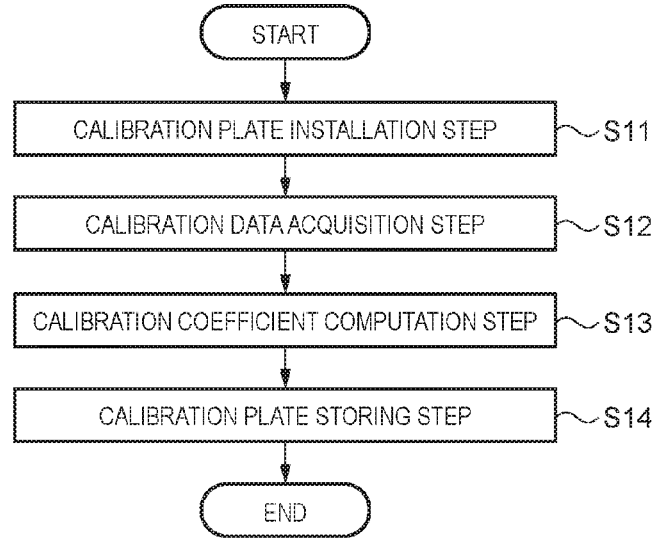
FIG. 6B is a flowchart representing a calibration plate measurement step (step S2) in detail.

FIG. 6B is a flowchart representing the calibration plate measurement step (step S2) in detail. In the flowchart of FIG. 6B, step S11 corresponds to a calibration plate installation step. This step moves the calibration plate 21 to the block position 45. The sequence then goes to step S12. Step S12 is a calibration data acquisition step. In this step, the measurement light 31 is applied to the calibration plate 21, and the first reflected light 32a is detected. The sequence then goes to step S13.

Step S13 is a calibration coefficient computation step. In this step, the light intensity of the first reflected light 32a is used to compute the calibration coefficient used in the object measurement step (step S3). The sequence then goes to step S14. Step S14 is a calibration plate storing step. In this step, the calibration plate 21 is moved to the storage position 46. This completes the calibration plate measurement step (step S2).

Figure 7:
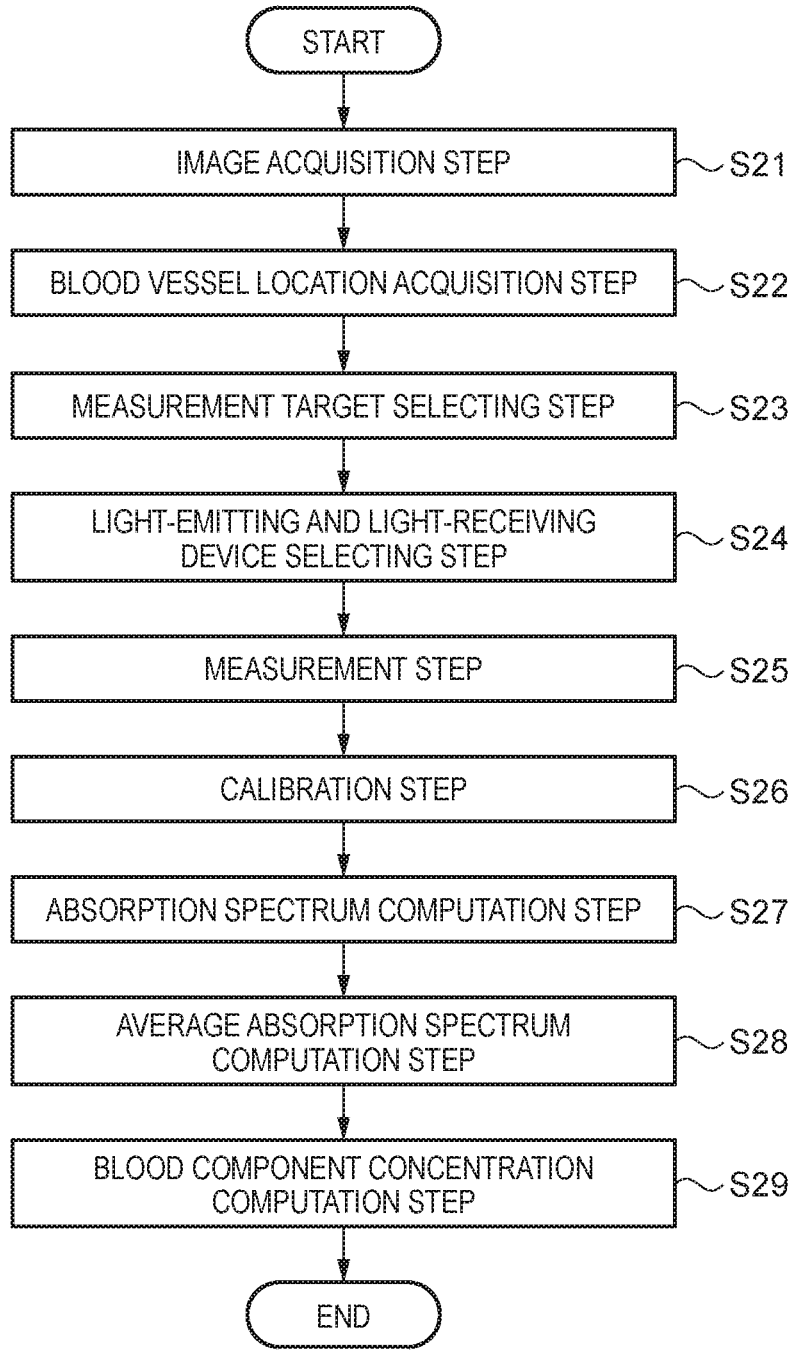
FIG. 7 is a flowchart representing an object measurement step (step S3) in detail.

FIG. 7 is a flowchart representing the object measurement step (step S3) in detail. In the flowchart of FIG. 7, step S21 corresponds to an image acquisition step. In this step, the biological image acquisition section 70 simultaneously turns on all the imaging light-emitting devices 27a, and the light-receiving devices 35 of the light-receiving layer 34 capture an image of the blood vessel 36. The sequence then goes to step S22. Step S22 is a blood vessel location acquisition step. In this step, the image captured by the measurement location arithmetic section 71 is used to acquire the location of the blood vessel 36. The sequence then goes to step S23.

Step S23 is a measurement target selecting step. In this step, a location suited for measurement is selected from the blood vessel 36 by the measurement location arithmetic section 71. The measurement location arithmetic section 71 also selects a reference measurement location. The sequence then goes to step S24. Step S24 is a light-emitting and light-receiving device selecting step. In this step, the measurement location arithmetic section 71 selects a measurement light-emitting device 27b and a light-receiving device 35 that are to be driven for the measurement. The measurement location arithmetic section 71 also selects a measurement light-emitting device 27b and a light-receiving device 35 that are to be driven for the acquisition of reference data. The sequence then goes to step S25.

Step S25 is a measurement step. In this step, the measurement light-emitting device 27b applies the measurement light 31 to the measured portion 2a, and the light intensity of the second reflected light 32b received by the light-receiving device 35 is measured. The sequence then goes to step S26. Step S26 is a calibration step. In this step, the light intensity measured by the calibration arithmetic section 73 is multiplied by the calibration coefficient. The sequence then goes to step S27. Step S27 is an absorption spectrum computation step. In this step, the absorption spectrum calculating section 74 computes the blood transmittance using the measurement result data. The sequence then goes to step S28. Step S28 is an average absorption spectrum computation step, in which the blood transmittances at different measurement locations are used to compute the mean transmittance value. The sequence then goes to step S29. Step S29 is a blood component concentration computation step. This step computes glucose concentration. This completes the object measurement step (step S3).

Figure 8A:
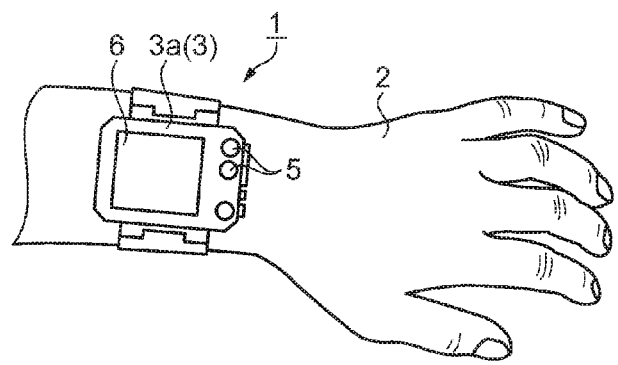
FIGS. 8A to 8D are schematic views explaining a biological information acquisition method.

FIG. 8A to FIG. 11D are schematic views explaining the biological information acquisition method. Referring to FIG. 8A to FIG. 11D, the biological information acquisition method is described below in detail, along with the corresponding steps described in FIGS. 6A to 7. FIG. 8A is a diagram corresponding to the apparatus installation step (step S1). As illustrated in FIG. 8A, an operator in step S1 installs the component measurement apparatus 1 on the subject 2. The component measurement apparatus 1 is installed with the back surface 3b in contact with the subject 2. The component measurement apparatus 1 is installed to make the touch panel 6 visible. The operator presses the operation switches 5 to start a measurement.

Figure 8B:
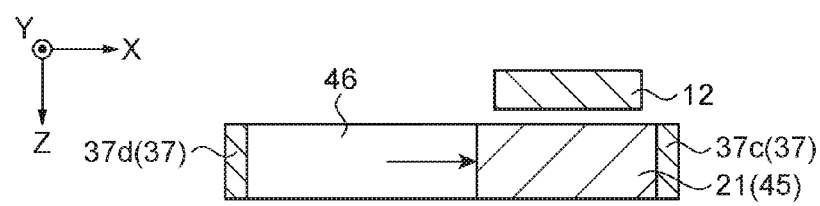

FIG. 8B is a diagram corresponding to the calibration plate installation step (step S11). As illustrated in FIG. 8B, the calibration plate control section 69 in step S11 outputs to the motor drive circuit 51 an instruction signal for moving the calibration plate 21 from the storage position 46 to the block position 45. The motor drive circuit 51 drives the motor 42 upon receiving the instruction signal. In response, the calibration unit 14 moves the calibration plate 21 from the storage position 46 to the block position 45. At the block position 45, the calibration plate 21 faces the sensor module 12, and blocks the light path of the second reflected light 32b. This prevents entry of the second reflected light 32b and other outside light into the sensor module 12.

Figure 8C:
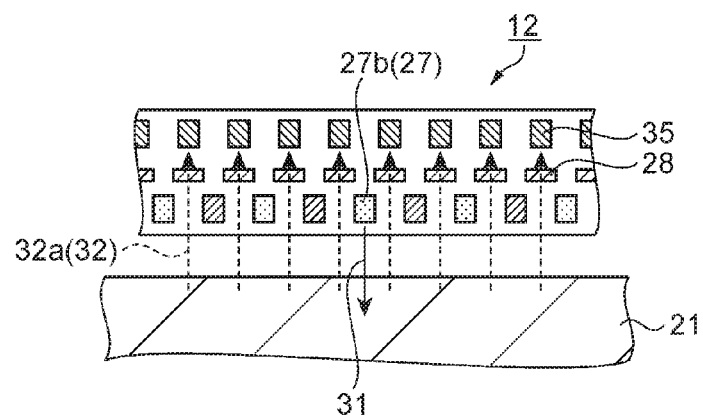
Figure 8D:
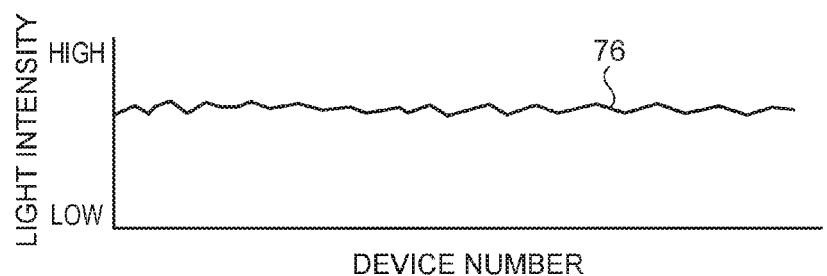

FIGS. 8C and 8D are diagrams corresponding to the calibration data acquisition step (step S12). As illustrated in FIG. 8C, in step S12, one of the measurement light-emitting devices 27b is turned on to irradiate the calibration plate 21. The measurement light 31 from the measurement light-emitting device 27b is reflected at the calibration plate 21, and becomes the first reflected light 32a. The first reflected light 32a irradiates the sensor module 12. The light-receiving devices 35 near the measurement light-emitting device 27b that has emitted light receive the first reflected light 32a, and detect its light intensity. Upon the light-receiving devices 35 detecting the light intensity, the measurement light-emitting device 27b is turned off, and another measurement light-emitting device 27b is turned on. In this manner, photodetection sensitivity data can be acquired for the combination of the activated measurement light-emitting device 27b and the light-receiving device 35.

The measurement light-emitting devices 27b are switched, and turned on one after another. The light-receiving devices 35 near the measurement light-emitting device 27b that has emitted light receive the first reflected light 32a, and detect its light intensity. In this manner, photodetection sensitivity data is acquired for all the measurement light-emitting devices 27b. In FIG. 8D, the vertical axis represents the light intensity detected by the light-receiving devices 35. The horizontal axis represents device number. The device number is a combination of the numbers for the measurement light-emitting devices 27b and the light-receiving devices 35.

The measurement light-emitting devices 27b and the light-receiving devices 35 each have designated numbers. For example, the device number (2,5) is assigned to data detected by the fifth light-receiving device 35 from the light emitted by the second measurement light-emitting device 27b. A sensitivity data line 76 represents an example of light intensities for different device number combinations. As represented by the sensitivity data line 76, light intensities corresponding to combinations of measurement light-emitting devices 27b and light-receiving devices 35 are measured, and stored as the calibration related data 61 in the memory 49. The sensitivity data line 76, shown as a line chart, may be stored in a tabular form by tabulating device number and light intensity.

In the calibration coefficient computation step (step S13), the calibration arithmetic section 73 computes the calibration coefficient. Prior to computation, a reference value of light intensity is set. Preferably, a reference value of light intensity is set using the light intensity received by a light-receiving device 35 of known performance under the measurement light 31 emitted by a measurement light-emitting device 27b of known performance.

The calibration arithmetic section 73 then divides the reference value by the light intensity of each device number to calculate the calibration coefficient. The calibration coefficient is 1 when the reference value and the detected light intensity have the same value. The calibration coefficient becomes smaller than 1 when the detected light intensity is larger than the reference value. The calibration coefficient becomes larger than 1 when the detected light intensity is smaller than the reference value.

FIG. 9A is a diagram corresponding to the calibration coefficient computation step (step S13). In FIG. 9A, the vertical axis represents calibration coefficient. The horizontal axis represents device number. A calibration coefficient line 77 represents an example of calibration coefficients for different device number combinations. As represented by the calibration coefficient line 77, calibration coefficients corresponding to combinations of measurement light-emitting devices 27b and light-receiving devices 35 are computed, and stored as the calibration related data 61 in the memory 49. The calibration coefficient line 77, shown as a line chart, may be stored in a tabular form by tabulating device number and calibration coefficient.

FIG. 9B is a diagram corresponding to the calibration plate storing step (step S14). As illustrated in FIG. 9B, the calibration plate control section 69 in step S14 outputs to the motor drive circuit 51 an instruction signal for moving the calibration plate 21 from the block position 45 to the storage position 46. The motor drive circuit 51 drives the motor 42 upon receiving the instruction signal. In response, the calibration unit 14 moves the calibration plate 21 from the block position 45 to the storage position 46. This permits the second reflected light 32b reflected at the measured portion 2a to enter the sensor module 12. This completes the calibration plate measurement step (step S2), and the sequence goes to the image acquisition step (step S21) representing the first step in the object measurement step (step S3).

In step S21, an image of the measured portion 2a is captured. The biological image acquisition section 70 outputs to the emission control section 66 an instruction signal for turning on the imaging light-emitting devices 27a. The emission control section 66 outputs to the sensor drive circuit the instruction signal for turning on the imaging light-emitting devices 27a. The sensor drive circuit 50 drives and turns on the imaging light-emitting devices 27a. The measurement light 31 emitted by the imaging light-emitting devices 27a irradiates the measured portion 2a.

The biological image acquisition section 70 outputs to the filter control section 68 an instruction signal for instructing the spectral devices 28 to pass light of 800 nm wavelength. The filter control section 68 outputs to the sensor drive circuit 50 an instruction signal for varying the wavelength characteristics of the spectral devices 28. The sensor drive circuit 50 drives the spectral devices 28, and sets an 800 nm wavelength for passage of light through the spectral devices 28. In this way, the blood vessel 36 absorbs the measurement light 31, and it becomes easier to capture an image of the blood vessel 36.

The biological image acquisition section 70 outputs to the photoreception control section 67 an imaging instruction signal. The photoreception control section 67 outputs to the sensor drive circuit 50 an instruction signal for driving the light-receiving devices 35. The sensor drive circuit 50 drives the light-receiving devices 35, and outputs the light intensity of the input light to the photoreception control section 67 after converting the light intensity into photoreception data. Because the light-receiving devices 35 are arrayed in a grid, the photoreception data forms a biological image 78. The photoreception control section 67 stores the biological image 78 as the biological image data 58 in the memory 49.

FIG. 9C is a diagram corresponding to the image acquisition step (step S21) and the blood vessel location acquisition step (step S22). The biological image 78 shown in FIG. 9C is an output image of the measured portion 2a from the sensor module 12. The biological image 78 is obtained as a two-dimensional image with pixels corresponding to the array of the light-receiving devices 35 in the sensor module 12. The blood vessel 36 more easily absorbs near-infrared rays than the non-blood vessel portion. Accordingly, the blood vessel image 78a, an image of the blood vessel 36, has lower luminance, and appears darker than the non-blood vessel image 78b of the non-blood vessel portion in the biological image 78. A blood vessel pattern can thus be extracted by extracting the lower luminance portion in the biological image 78. Specifically, the presence or absence of the blood vessel 36 directly below the light-receiving device 35 can be determined by determining whether the luminance of the corresponding pixel constituting the biological image 78 has a value that is equal to or less than a predetermined threshold value. This makes it possible to detect the location of the blood vessel 36.

FIG. 9D is a diagram corresponding to the measurement target selecting step (step S23), schematically representing blood vessel location information obtained from the biological image 78. The blood vessel location information is information indicative of whether the location corresponding to each pixel of the biological image 78 is the blood vessel 36 or the non-blood vessel portion 81. In step S23, the measurement location arithmetic section 71 selects a measurement site 82, a measurement location of the blood vessel 36. The measurement location arithmetic section 71 selects the measurement site 82 by satisfying the following selection conditions. The measurement site 82 satisfies the selection conditions when it is not a branching or a merging portion of the blood vessel, or an end portion of the image, and has a predetermined length and width.

At branching and merging portions 36a of the blood vessel, the reflected light 32 has the possibility of mixing with light that has passed through a blood vessel 36 that is not a measurement target. The light that has passed through a blood vessel 36 that is not a measurement target has the possibility of affecting the absorption spectrum of the measurement site 82 selected as the measurement target. This may result in poor measurement accuracy. The measurement site 82 is thus selected from portions other than the branching and merging portions 36a of the blood vessel 36.

At end portions 36b of the blood vessel 36 in the biological image 78, there is no information about the blood vessel structure in the vicinity of the outer side of the image, whether the blood vessel is branched or merging. For the same reason described above, the measurement site 82 is thus selected from portions of blood vessel 36 other than the end portions 36b of the biological image 78 to avoid the possibility of lowering measurement accuracy.

Figure 10A:
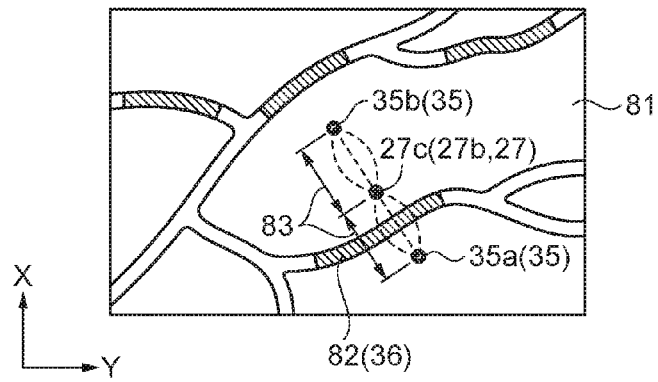
FIGS. 10A to 10C are schematic views explaining the biological information acquisition method.

FIG. 10A is a diagram corresponding to the light-emitting and light-receiving device selecting step (step S24). As illustrated in FIG. 10A, the measurement location arithmetic section 71 in step S24 selects a measurement light-emitting device 27b and a light-receiving device 35 that are to be driven for measurement. Here, a measurement light-emitting device 27b and a light-receiving device 35 are selected so that the measurement site 82 is between the measurement light-emitting device 27b and the light-receiving device 35. The light-receiving device 35 detects light that has passed through the measurement site 82.

The measurement location arithmetic section 71 also selects a measurement light-emitting device 27b and a light-receiving device 35 that are to be driven for reference measurement. Here, a measurement light-emitting device 27b and a light-receiving device 35 are selected so that the measurement site 82 is not between the measurement light-emitting device 27b and the light-receiving device 35. The light-receiving device 35 detects light that did not pass through the measurement site 82. This measurement will be referred to as reference measurement. In the present embodiment, the same light-emitting device 27 is set for the measurement and the reference measurement at the same location.

Assume here that the measurement light-emitting device 27b at the irradiation position is a light-emitting device 27c, and the light-receiving device 35 at the reception position for measurement is a measurement light-receiving device 35a. The measurement location arithmetic section 71 sets locations for the light-emitting device 27c and the measurement light-receiving device 35a so that the measurement site 82 is centered between the light-emitting device 27c and the measurement light-receiving device 35a. The measurement location arithmetic section 71 also sets locations for the light-emitting device 27c and the measurement light-receiving device 35a so that the distance between the light-emitting device 27c and the measurement light-receiving device 35a becomes a predetermined optimum distance 83.

Assume here that the light-receiving device 35 at the reference reception position for reference measurement is a reference light-receiving device 35b. The light-emitting device 27 at the irradiation posit ion for reference measurement is the light-emitting device 27c. The location for the reference light-receiving device 35b is set so that the blood vessel 36 does not exist between the light-emitting device 27c and the reference light-receiving device 35b. The locations for the light-emitting device 27c and the reference light-receiving device 35b are set so that the distance between the light-emitting device 27c and the reference light-receiving device 35b becomes the predetermined optimum distance 83.

Figure 10B:
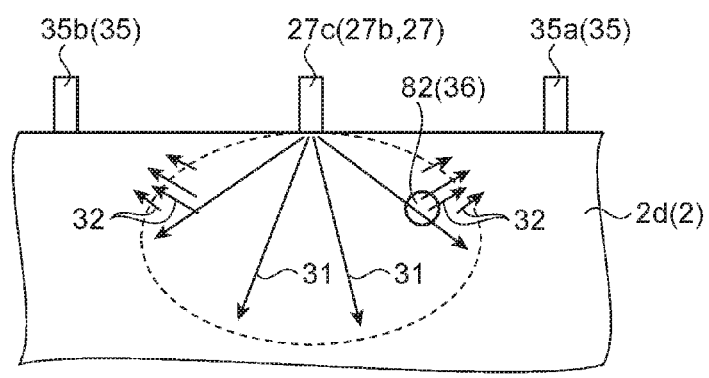
Figure 10C:
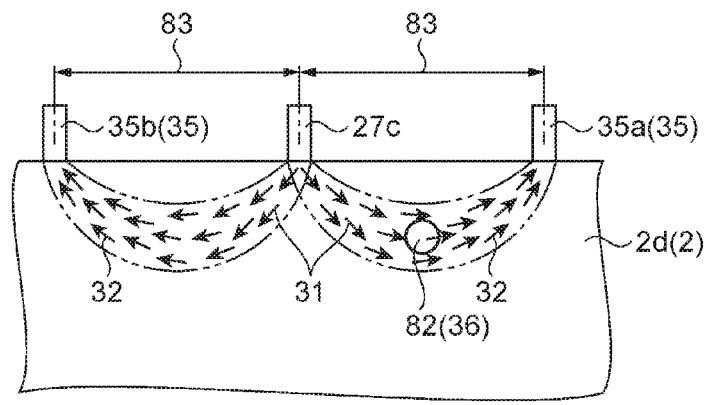

FIGS. 10B and 10C are diagrams corresponding to the measurement step (step S25). These are schematic cross sectional views taken in depth direction, explaining propagation of light inside the body tissue. As illustrated in FIG. 10B, the light-emitting device 27c in step S25 emits measurement light 31 in a predetermined directional characteristic. The cellular tissue surrounding the blood vessel 36 in the subject 2 represents a common tissue 2d. The common tissue 2d is a cellular tissue including, for example, skin tissue, adipose tissue, and muscle tissue, surrounding the blood vessel 36 being measured. Some of the measurement light 31 pass through the blood vessel 36 through the common tissue 2d. Some of the measurement light 31 pass through the blood vessel 36 after being scattered by the common tissue 2d. Some of the measurement light 31 pass through the blood vessel 36, and enter the measurement light-receiving device 35a as reflected light 32. Some of the measurement light 31 enter the measurement light-receiving device 35a and the reference light-receiving device 35b as reflected light 32, without passing through the blood vessel 36.

FIG. 10C is a diagram simulating the paths of light rays emitted by the light-emitting device 27 and entering the light-receiving devices 35, using a ray tracing method. As illustrated in FIG. 10C, the measurement light 31 radiating from the light-emitting device 27c undergoes diffuse reflection inside the body tissue, and some of the radiating light reaches the light-receiving devices 35. The light paths of the propagating light travel through banana-shaped regions confined between two arcs. The light path is widest along the depth direction near substantially the center between the light-emitting device 27 and the light-receiving device 35. The light path is also deepest in this part of the tissue. The reachable light depth increases as the distance between the light-emitting device 27 and the light-receiving device 35 increases.

For improved measurement accuracy, it is desirable that the light-receiving device 35 receives more transmitted light from the blood vessel 36. For this reason, it is desirable to locate the measurement target, or the measurement site 82, at substantially the center between the light-emitting device 27 and the light-receiving device 35. The optimum distance 83 is specified according to the supposed depth of the measurement site 82. The optimum distance 83 representing the optimum interval between the light-emitting devices 27 and the light-receiving devices 35 is about two times the depth of the blood vessel 36 from skin surface. For example, the optimum distance 83 is about 5 to 6 mm for a depth of about 3 mm.

The wavelength of the measurement light 31 emitted by the light-emitting device 27c is such that the absorbance varies with blood glucose levels. Some of the reflected light 32 detected by the measurement light-receiving device 35a pass through the blood vessel 36, and some of the reflected light 32 is absorbed by blood in the blood vessel 36. Accordingly, the output data from the measurement light-receiving device 35a contains information about the blood absorbance and the absorbance of the non-blood vessel portion 81. On the other hand, the reflected light 32 detected by the reference light-receiving device 35b does not pass through the blood vessel 36, and is not absorbed by blood in the blood vessel 36. Accordingly, the output data from the reference light-receiving device 35b contains information about the absorbance of the non-blood vessel portion 81.

Figure 11A:
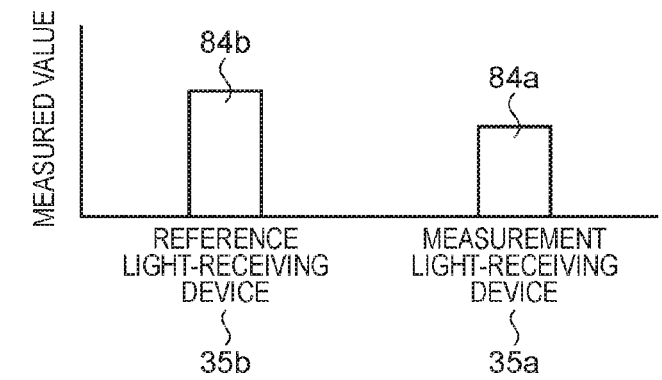
FIGS. 11A to 11D are schematic views explaining the biological information acquisition method.
Figure 11B:
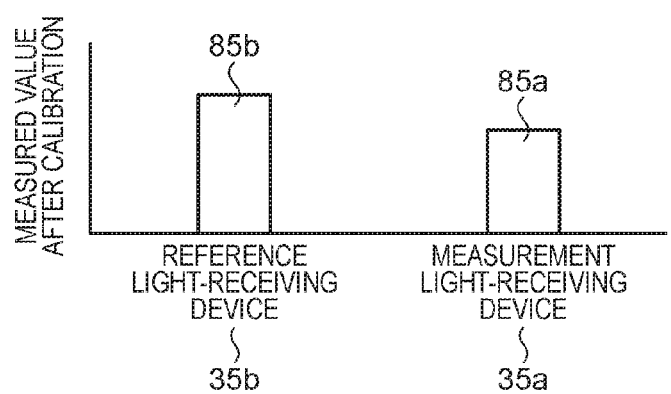

FIGS. 11A and 11B are diagrams corresponding to the calibration step (step S26). In FIG. 11A, the vertical axis represents measured value, specifically the light intensity value detected by the light-receiving device 35. The light intensity on vertical axis becomes higher from the bottom to top. The horizontal axis depicts the measurement light-receiving device 35a and the reference light-receiving device 35b. The measured values by the measurement light-receiving device 35a and the reference light-receiving device 35b are presented as a bar chart. The measured values detected by the measurement light-receiving device 35a and the reference light-receiving device 35b are given as blood measurement value 84a and reference measurement value 84b, respectively.

In step S26, the calibration arithmetic section 73 multiplies the measured value by the calibration coefficient. The calibration coefficient is the coefficient calculated by the calibration arithmetic section 73 in step S2. The calibration coefficient is set for each combination of the light-emitting device 27 and the light-receiving device 35. In FIG. 11B, the vertical axis represents measured value after calibration, specifically value after the calibration of the light intensity value detected by the light-receiving device 35. The light intensity on vertical axis becomes higher from the bottom to top. The horizontal axis depicts the measurement light-receiving device 35a and the reference light-receiving device 35b. The calibrated blood measurement value 85a and the calibrated reference measurement value 85b are presented as a bar chart.

In this step, the blood measurement value 84a is multiplied by the calibration coefficient corresponding to the combination of the light-emitting device 27c and the measurement light-receiving device 35a to calculate the calibrated blood measurement value 85a. The calibrated reference measurement value 85b is calculated by multiplying the reference measurement value 84b by the calibration coefficient corresponding to the combination of the light-emitting device 27c and the reference light-receiving device 35b.

The light-emitting devices 27 and the light-receiving devices 35 have performance variance attributed to production. There is also a performance change due to changes with time. In step S2, the calibration coefficient is set with the use of the calibration plate 21 having a reflectance that is uniform throughout the plane and that does not easily undergo changes. In step S26, the measured values are calibrated with the calibration coefficient. The calibrated blood measurement value 85a and the calibrated reference measurement value 85b obtained in step S26 are thus unlikely to be affected by changes occurring in the light-emitting devices 27 and the light-receiving devices 35 over time, or by the production variance of the light-emitting devices 27 and the light-receiving devices 35.

In the absorption spectrum computation step (step S27), the transmittance through the blood vessel 36 is computed with the calibrated blood measurement value 85*a* and the calibrated reference measurement value 85*b*. The transmittance may be calculated through four arithmetic operations of the calibrated blood measurement value 85*a* and the calibrated reference measurement value 85*b*. In a simpler operation, the calibrated blood measurement value 85*a* may be divided by the calibrated reference measurement value 85*b* to obtain a transmittance. The operation of the calibrated blood measurement value 85*a* may take into account the proportion that passed through the blood vessel 36. The proportion of light that passed through the blood vessel 36 may be calculated using methods such as a phantom method, and a Monte Carlo simulation method.

In the average absorption spectrum computation step (step S28), the mean value is computed using a plurality of transmittance values. Step S25 has been described through the case of a measurement at a single measurement location. The mean value is computed in step S28 when there is more than one measurement location. The moving average may be computed when performing measurements at predetermined time intervals. Step S28 may be omitted when the mean is not computed.

Figure 11C:
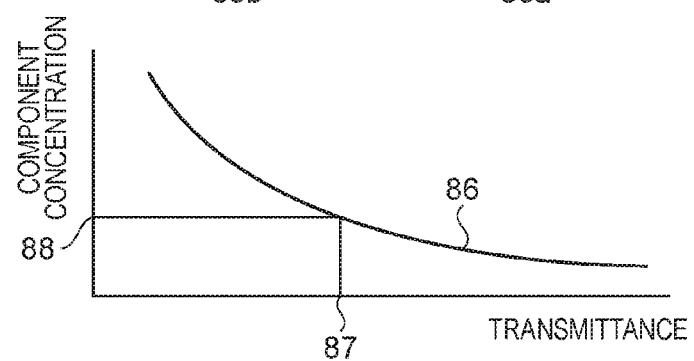

FIG. 11C is a diagram corresponding to the blood component concentration computation step (step S29). In step S29, the calculated transmittance is used to compute blood glucose concentration. In FIG. 11C, the vertical axis represents blood glucose concentration. The concentration is higher from the bottom to top of the diagram. The horizontal axis represents transmittance, representing the blood transmittance rate of light of the same wavelength as the wavelength of the measurement light 31. In the diagram, the transmittance increases from the left to right. A correlation curve 86 represents the relationship between blood transmittance and blood glucose concentration. Absorption of light increases with increase of blood glucose concentration, and the transmittance decreases. When the mean value calculated in the step S28 is a calculated transmittance value 87, the correlation curve 86 is used to calculate an arithmetic concentration value 88 representing blood glucose concentration. The correlation curve 86 may be represented as a function, or as a correlation table in a tabular form. The arithmetic concentration value 88 can be calculated from the calculated transmittance value 87 also in these cases. This completes the object measurement step (step S3), and the sequence goes to step S4.

In the warning determination step (step S4), the arithmetic concentration value 88 is compared to determination values. The determination values include an upper determination value and a lower determination value. The current state is determined as normal, and not in need of a warning when the arithmetic concentration value 88 is between the upper determination value and the lower determination value. The current state is determined as abnormal when the arithmetic concentration value 88 is higher than the upper determination value. The current state is also determined as abnormal when the arithmetic concentration value 88 is below the lower determination value. In an abnormal state, it is determined to give a warning, and the sequence goes to step S5.

Figure 11D:
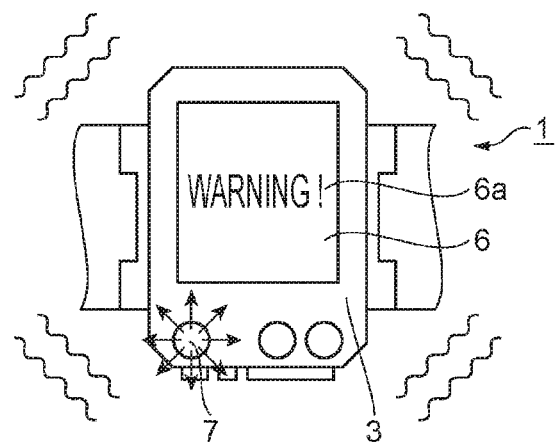

FIG. 11D is a diagram corresponding to the warning step (step S5). As illustrated in FIG. 11D, the subject 2 is warned in step S5. The touch panel 6 displays a warning text 6*a*. The warning text 6*a* contains a statement explaining that the subject 2 is at risk. The subject 2 reading the statement can easily understand his or her status. The speaker 7 produces a warning sound. Warning sound data are prestored in the memory 49, and the CPU 48 outputs to the speaker 7 a voltage waveform based on the warning sound data. The speaker 7 outputs sound after converting the voltage waveform into a sound wave. The subject 2 also can be brought to attention even when he or she is not looking at the touch panel 6. The CPU 48 vibrates the caseback 13 by driving the vibrator 18. Because the caseback is in contact with the subject 2, the vibration is transmitted to the subject 2. The subject 2 can then be brought to attention that he or she is in an abnormal state.

In the end determining step (step S6), it is determined whether to end the acquisition of blood glucose concentration information. It is determined to end the acquisition upon the operator operating the operation switches 5 or the operation input section 26, and giving an instruction to end the acquisition of blood glucose concentration information. Steps S2 to S6 are repeated when the operator does not give an instruction to end the acquisition. The calibration plate measurement step (step S2) and the object measurement step (step S3) are thus repeatedly performed with the component measurement apparatus 1 installed on the subject 2. Blood glucose concentration changes in the subject 2 can be detected even when the subject 2 is moving.

In the apparatus removal step (step S7), the component measurement apparatus 1 is removed from the subject 2. This completes the acquisition of glucose concentration information from the subject 2.

As described above, the present embodiment has the following effects.

(1) According to the present embodiment, the calibration unit 14 moves the calibration plate 21 to switch the reflected light 32 that enters the light-receiving layer 34. The calibration unit 14 enters either the second reflected light 32*b* reflected at the measured portion 2*a*, or the first reflected light 32*a* reflected at the calibration plate 21 to the light-receiving layer 34. Upon receiving the second reflected light 32*b*, the light-receiving layer 34 outputs a signal corresponding to the light intensity of the second reflected light 32*b*. Upon reflecting light, the measured portion 2*a* absorbs light of specific wavelengths that vary with the components of the measured portion 2*a*. Information concerning the components of the measured portion 2*a* can thus be acquired by analyzing the output light intensity of the second reflected light 32*b* from the light-receiving layer 34.

The light intensity of the measurement light 31 applied to the measured portion 2*a* and the calibration plate 21 varies with time, and the rate at which the light-receiving layer 34 converts the reflected light 32 into a signal also varies with time. Upon the calibration unit 14 entering the first reflected light 32*a* to the light-receiving layer 34, the light-receiving layer 34 outputs a signal corresponding to the light intensity of the reflected light 32 at the calibration plate 21. The components of the calibration plate 21 do not easily undergo changes. This makes it possible to find the effect of changes occurring in the measurement light 31, or in the sensitivity of the light-receiving layer 34. The detected light intensity of the first reflected light 32*a* at the calibration plate 21, and the detected light intensity of the second reflected light 32*b* at the measured portion 2*a* can thus be used to accurately detect the characteristics of the reflected light 32 at the measured portion 2*a*.

(2) According to the present embodiment, when entering the second reflected light 32*b* to the light-receiving layer 34, the calibration unit 14 moves the calibration plate 21 to the storage position 46. The light path of the second reflected light 32b is not blocked at the storage position 46. The second reflected light 32b can thus enter the light-receiving layer 34 without being blocked by the calibration plate 21.

(3) According to the present embodiment, when entering the first reflected light 32a to the light-receiving layer 34, the calibration unit 14 moves the calibration plate 21 to the block position 45. The block position 45 blocks the light path of the second reflected light 32b. The first reflected light 32a can thus enter the light-receiving layer 34, whereas the second reflected light 32b is blocked from entry.

(4) According to the present embodiment, the calibration arithmetic section 73 calibrates the light intensity signal of the second reflected light 32b using the light intensity signal of the first reflected light 32a. The first reflected light 32a represents the reflected light 32 off the calibration plate 21 into the light-receiving layer 34. The second reflected light 32b represents the reflected light 32 reflected at the measured portion 2a. The calibration arithmetic section 73 can thus clearly distinguish the measured portion 2a against the calibration plate 21. Time-dependent changes occurring in the light-emitting layer 29 irradiating the calibration plate 21 and the measured portion 2a, and in the light-receiving layer 34 can thus have reduced effects in analyzing the second reflected light 32b.

(5) According to the present embodiment, the light-emitting devices 27 and the light-receiving devices 35 have optical axes in the same direction. In the sensor module 12, the direction with a high emission quantity and the direction with the highest photoreception sensitivity are the same. The sensor module 12 can thus receive the first reflected light 32a with good sensitivity with the calibration plate 21 installed in the direction of the optical axes of the light-emitting devices 27 and the light-receiving devices 35. Likewise, the sensor module 12 can receive the second reflected light 32b with good sensitivity with the measured portion 2a placed in the direction of the optical axes of the light-emitting devices 27 and the light-receiving devices 35.

(6) According to the present embodiment, the calibration plate 21 contains polytetrafluoroethylene. Polytetrafluoroethylene reflects near-infrared light without absorbing it. This makes it possible to efficiently obtain the first reflected light 32a used for calibration.

(7) According to the present embodiment, the calibration plate control section 69 controls the calibration unit 14. The calibration unit 14 switches the first reflected light 32a and the second reflected light 32b for entry into the sensor module 12 under the control of the calibration plate control section 69. The entry of the first reflected light 32a and the second reflected light 32b can thus be switched depending on the situation, without being operated by the subject 2.

(8) According to the present embodiment, the light intensity detection of the first reflected light 32a, the light intensity detection of the second reflected light 32b, and the computation of blood glucose concentration are repeated with the component measurement apparatus 1 installed on the subject 2. Blood glucose concentration changes in the subject 2 can thus be detected even when the subject 2 is moving.

Second Embodiment

Figure 12A:
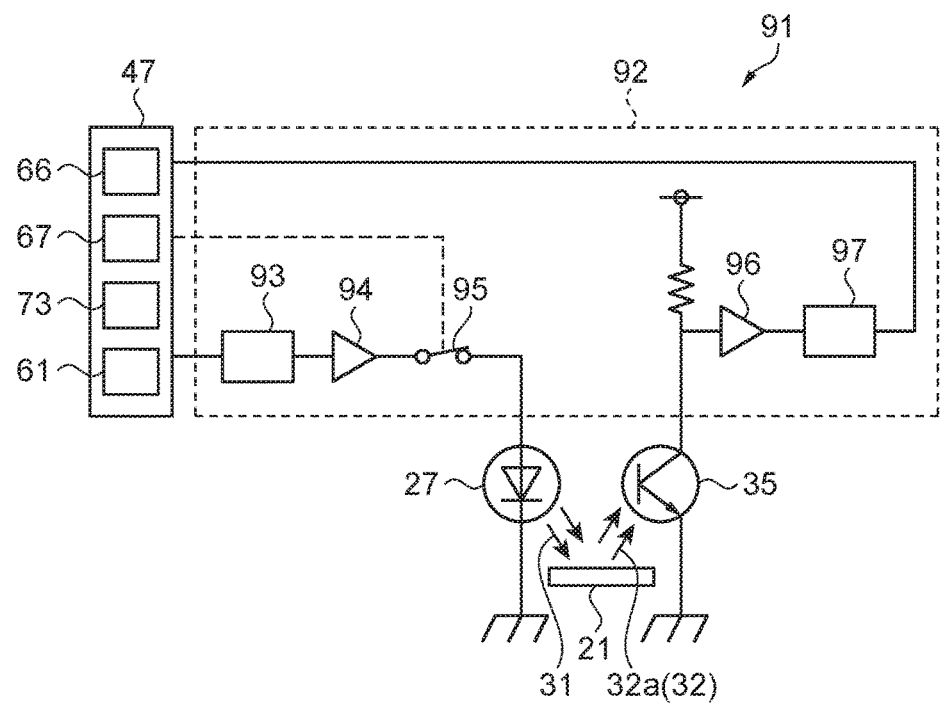
FIG. 12A is a block diagram representing a relevant portion of a sensor drive circuit according to Second Embodiment.
Figure 12B:
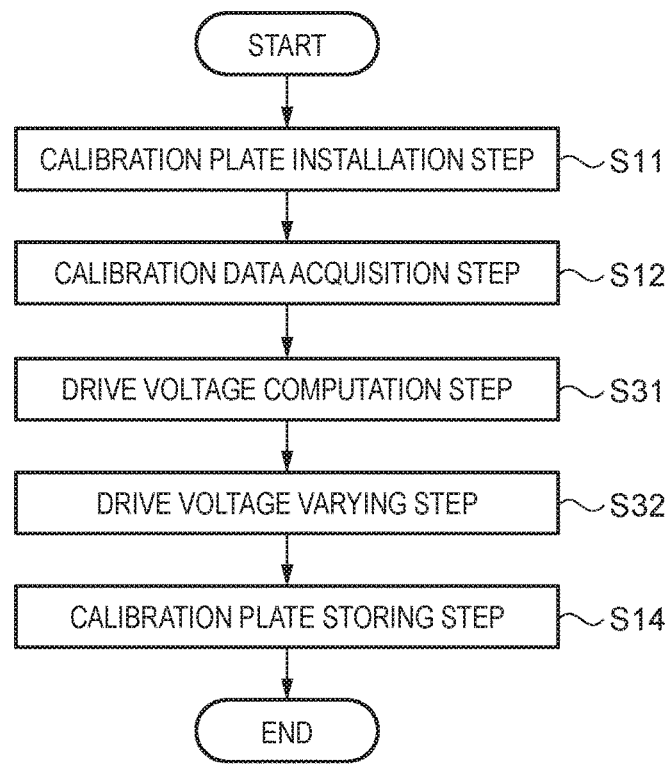
FIG. 12B is a flowchart representing a calibration plate measurement step (step S2) in detail.
Figure 13:
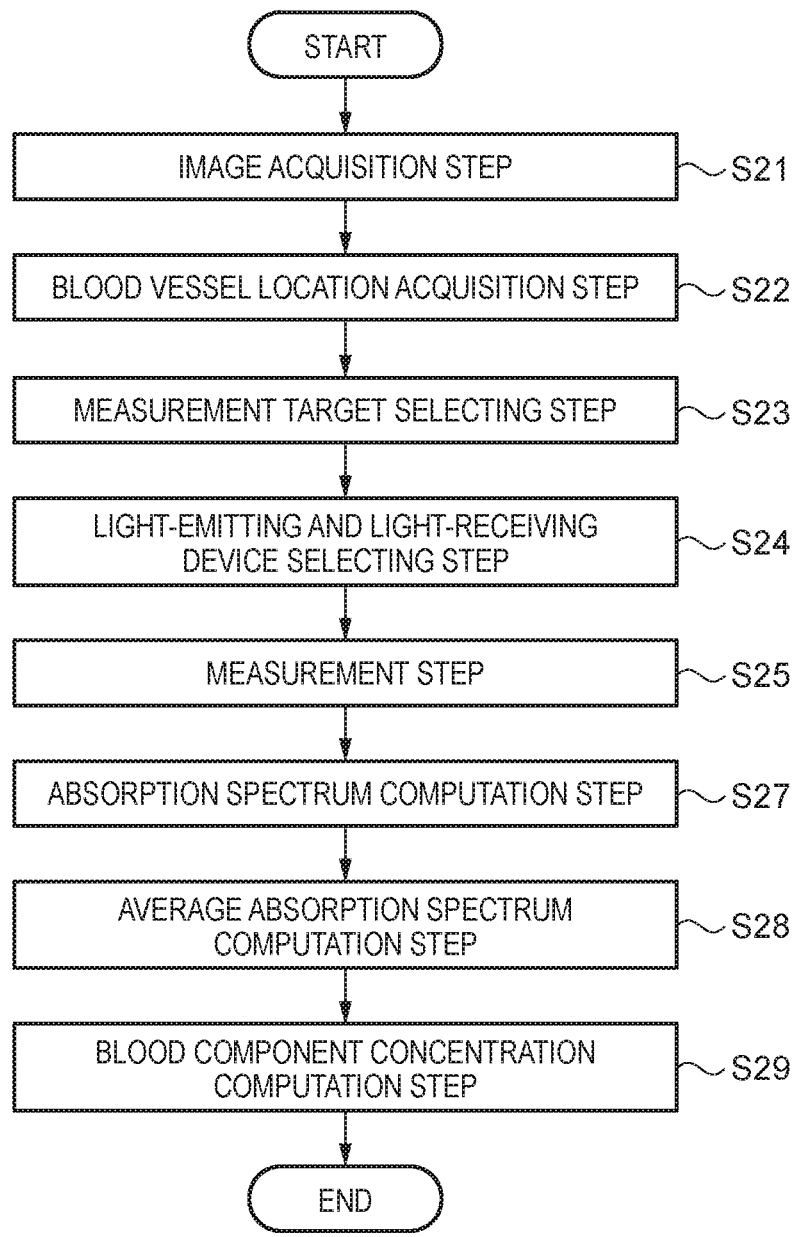
FIG. 13 is a flowchart representing an object measurement step (step S3) in detail.

An embodiment of the component measurement apparatus is described below with reference to FIGS. 12A and 12B, and FIG. 13. FIG. 12A is a block diagram representing a relevant portion of a sensor drive circuit according to Second Embodiment, and FIG. 12B is a flowchart representing a calibration plate measurement step (step S2) in detail. FIG. 13 is a flowchart representing an object measurement step (step S3) in detail. The present embodiment differs from First Embodiment in that the value measured with the calibration plate 21 is used to adjust the output of the light-emitting device 27c. The same features already described in First Embodiment will not be described further.

Specifically, in the present embodiment, a sensor drive circuit 92 connected to the controller 47 is installed in a component measurement apparatus 91 (information acquisition apparatus), as shown in FIG. 12A. The sensor drive circuit 92 drives the light-emitting devices 27, the spectral devices 28, and the light-receiving devices 35. The controller 47 has an emission control section 66, a photoreception control section 67, and a calibration arithmetic section 73 to realize its functions. The controller 47 also has a region in memory 49 where calibration related data 61 is stored. The sensor drive circuit 92 includes a first D/A (Digital/Analog) converter 93, a first amplifier 94, and a switch section 95.

The controller 47 and the first D/A converter 93 are connected to each other, and the first D/A converter 93, the first amplifier 94, and the switch section 95 are connected in this order. The switch section 95 is connected to the light-emitting device 27. The first D/A converter 93, the first amplifier 94, and the switch section 95 are provided in the same number as the number of light-emitting devices 27. A different applied voltage may be set for each different light-emitting device 27. The sensor drive circuit 92 also includes a second amplifier 96, and an A/D (Analog/Digital) converter 97. The light-receiving devices 35, the second amplifier 96, the A/D converter 97, and the controller 47 are connected in this order.

The calibration related data 61 includes drive voltage data for driving the light-emitting devices 27. The emission control section 66 receives drive voltage data for the light-emitting device 27 from the calibration related data 61, and outputs the data to the first D/A converter 93. The first D/A converter 93 converts the voltage data into a voltage signal, and outputs the signal to the first amplifier 94. The first amplifier 94 receives the voltage data, and outputs it to the switch section 95 after amplifying the power. The switch section 95 receives the instruction signal from the emission control section 66, and the power amplified voltage signal. The switch section 95 then outputs to the light-emitting device 27 a voltage waveform corresponding to the instruction signal. This drives the light-emitting device 27 according to the voltage instructed by the emission control section 66. The light-emitting device 27 emits the measurement light 31. In step S2, the measurement light 31 is applied to the calibration plate 21.

The first reflected light 32a reflected at the calibration plate 21 enters the light-receiving device 35. The light-receiving device 35 converts the light intensity of the first reflected light 32a into voltage, and outputs the voltage signal to the second amplifier 96. The second amplifier 96 amplifies the input voltage signal, and outputs it to the A/D converter 97. The A/D converter 97 converts the voltage signal into voltage data, and outputs it to the controller 47. In the controller 47, the CPU 48 stores the corresponding voltage data of the first reflected light 32a in the memory 49.

In FIG. 12B, steps S11 and S12 are the same as in First Embodiment, and will not be described. The sequence goes to step S31 after step S12. In the drive voltage computation step (step S31), the calibration arithmetic section 73 computes a drive voltage for the light-emitting device 27. Prior to computation, a reference value is set for the voltage corresponding to the light intensity received by the light-receiving device 35. The reference value includes an upper-limit reference value corresponding to the upper-limit light intensity, and a lower-limit reference value corresponding to the lower-limit light intensity. The calibration arithmetic section 73 receives from the memory 49 voltage data corresponding to the first reflected light 32a detected in step S12.

The calibration arithmetic section 73 then compares the corresponding voltage data of the first reflected light 32a with the reference value. The drive voltage data driving the light-emitting device 27 is decreased when the voltage data exceeds the upper-limit reference value. The drive voltage data driving the light-emitting device 27 is increased when the voltage data is below the lower-limit reference value. The drive voltage data is varied over a range that is proportional to the difference between the voltage data and the reference value. The calibration arithmetic section 73 compares the corresponding voltage data of the first reflected light 32a with the reference value for all the light-emitting devices 27, and varies the drive voltage data when the voltage data is larger than the upper-limit reference value and when the voltage data is smaller than the lower-limit reference value. The sequence then goes to step S32.

In the drive voltage varying step (step S32), the drive voltage data varied in step S31 is stored in the memory 49. This varies the drive voltage data stored in the memory 49. The sequence then goes to step S14.

In FIG. 13, steps S21 to S25 are the same as in First Embodiment, and will not be described. The sequence goes to step S27 (absorption spectrum computation step) after step S25. The calibration step (step S26) is omitted. Step S26 can be omitted because the drive voltage for the light-emitting device 27 is varied in steps S31 and S32. Steps S27 to S29 are the same as in First Embodiment, and will not be described.

As described above, the present embodiment has the following effects.

(1) According to the present embodiment, the voltage driving the light-emitting device 27 is calibrated when there is a performance change in the light-emitting devices 27 and the light-receiving devices 35. The output voltage data from the sensor drive circuit 92 to the controller 47 can thus accurately reflect the state of the measured portion 2a.

(2) According to the present embodiment, the voltage driving the light-emitting device 27 is increased when there is a performance drop in the light-emitting devices 27 and the light-receiving devices 35. This increases the light intensity of the measurement light 31, and can suppress decrease of the SN ratio (signal Noise) in the output voltage data to the controller 47.

Third Embodiment

Figure 14A:
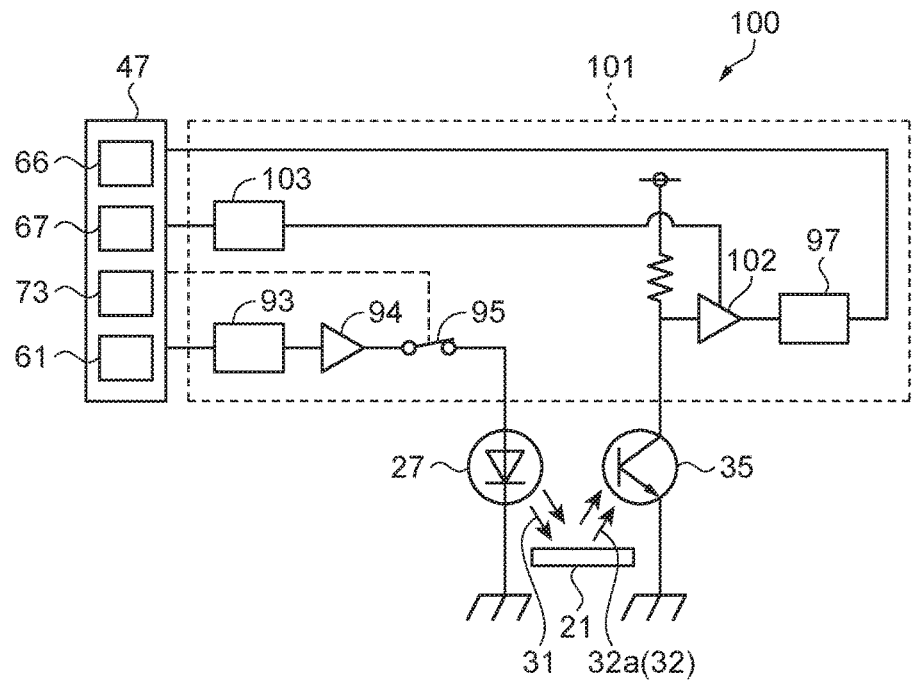
FIG. 14A is a block diagram representing a relevant portion of a sensor drive circuit according to Third Embodiment.
Figure 14B:
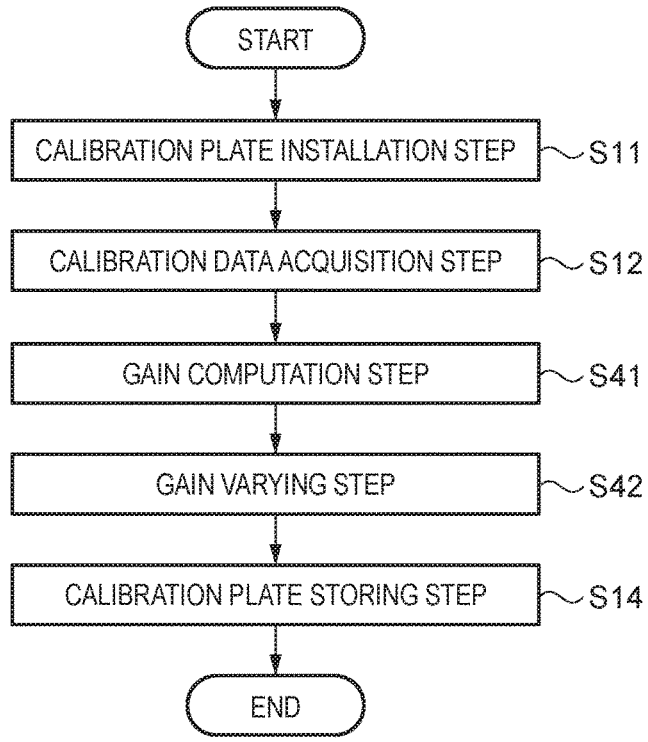
FIG. 14B is a flowchart representing a calibration plate measurement step (step S2) in detail.

An embodiment of the component measurement apparatus is described below with reference to FIGS. 14A and 14B. FIG. 14A is a block diagram representing a relevant portion of a sensor drive circuit. FIG. 14B is a flowchart representing a calibration plate measurement step (step S2) in detail. The present embodiment differs from First Embodiment in that the value measured with the calibration plate 21 is used to adjust the amplification gain for the output of the light-receiving device 35. The same features already described in First and Second Embodiments will not be described further.

Specifically, in the present embodiment, a sensor drive circuit 101 connected to the controller 47 is installed in a component measurement apparatus 100 (information acquisition apparatus), as shown in FIG. 14A. The sensor drive circuit 101 drives the light-emitting devices 27, the spectral devices 28, and the light-receiving devices 35. The controller 47 has an emission control section 66, a photoreception control section 67, and a calibration arithmetic section 73 to realize its functions. The controller 47 also has a region in memory 49 where calibration related data 61 is stored.

The sensor drive circuit 101 includes a first D/A converter 93, a first amplifier 94, and a switch section 95. The controller 47 and the first D/A converter 93 are connected to each other, and the first D/A converter 93, the first amplifier 94, and the switch section 95 are connected in this order. The switch section 95 is connected to the light-emitting device 27. The first D/A converter 93, the first amplifier 94, and the switch section 95 are provided in the same number as the number of light-emitting devices 27. A different applied voltage may be set for each different light-emitting device 27. The sensor drive circuit 101 also includes a second amplifier 102, a second D/A converter 103, and an A/D converter 97. The light-receiving device 35, the second amplifier 102, the A/D converter 97, and the controller 47 are connected in this order. The second amplifier 102 has a variable gain, and is connected to the controller 47 via the second D/A converter 103.

In step S2, the measurement light 31 is applied to the calibration plate 21. The first reflected light 32a reflected at the calibration plate 21 enters the light-receiving device 35. The light-receiving device 35 converts the light intensity of the first reflected light 32a into voltage, and outputs the voltage signal to the second amplifier 102. The second amplifier 102 amplifies the input voltage signal, and outputs it to the A/D converter 97. The A/D converter 97 converts the voltage signal into voltage data, and outputs it to the controller 47. In the controller 47, the CPU 48 stores the corresponding voltage data of the first reflected light 32a in the memory 49.

The calibration related data 61 includes gain data for the second amplifier 102. The photoreception control section 67 outputs the gain data to the second D/A converter 103. The second D/A converter 103 converts the gain data into a voltage signal indicative of a gain, and outputs it to the second amplifier 102. The second amplifier 102 receives the voltage signal indicative of a gain, and amplifies the corresponding voltage signal of the first reflected light 32a with the instructed gain. The second amplifier 102 amplifies the input voltage signal, and outputs it to the A/D converter 97.

In FIG. 14B, steps S11 and S12 are the same as in First Embodiment, and will not be described. The sequence goes to step S41 after step S12. In the gain computation step (step S41), the calibration arithmetic section 73 computes a gain of the second amplifier 102. Prior to computation, a reference value is set for the output voltage of the second amplifier 102 corresponding to the light intensity received by the light-receiving device 35. The reference value includes an upper-limit reference value corresponding to the upper-limit light intensity, and a lower-limit reference value corresponding to the lower-limit light intensity. The calibration arithmetic section 73 receives from the memory 49 voltage data corresponding to the first reflected light 32a detected in step S12.

The calibration arithmetic section 73 then compares the corresponding voltage data of the first reflected light 32a with the reference value. The gain data indicative of the gain of the second amplifier 102 is decreased when the voltage data exceeds the upper-limit reference value. The gain data is increased when the voltage data is below the lower-limit reference value. The gain data is varied over a range that is proportional to the difference between the voltage data and the reference value. As a result, the voltage data corresponding to the first reflected light 32a takes the same value as the reference value. The calibration arithmetic section 73 compares the corresponding voltage data of the first reflected light 32a with the reference value for all the light-receiving devices 35, and varies the gain data when the voltage data is larger than the upper-limit reference value and when the voltage data is smaller than the lower-limit reference value. In this manner, the gain data is varied so that the voltage data corresponding to the first reflected light 32a takes the same value as the reference value in all the light-receiving devices 35. The sequence then goes to step S42.

In the gain varying step (step S42), the gain data varied in step S41 is stored in the memory 49. This varies the gain data stored in the memory 49. The sequence then goes to step S14. In the object measurement step (step S3), the calibration step (step S26) is omitted, as in Second Embodiment.

As described above, the present embodiment has the following effect.

(1) According to the present embodiment, the gain of the second amplifier 102 is varied when there is a performance change in the light-emitting devices 27 and the light-receiving devices 35. The output voltage data from the sensor drive circuit 101 to the controller 47 can thus accurately reflect the state of the measured portion 2a.

The present embodiment is not limited to the description of the embodiments above, but may be altered or modified in many ways by a person with ordinary skill in the art within the technical idea of the invention. Variations are described below.

Variation 1

In the foregoing First Embodiment, the computed blood component is glucose concentration. However, this should not be construed as a limitation, and blood oxygen concentration may be measured using the transmittance of hemoglobin. Hemoglobin can be detected with measurement light 31 of about 650 nm wavelength. A wavelength of about 650 nm is thus set for passage of reflected light 32 through the spectral devices 28. The transmittance can then be computed to measure blood oxygen concentration. Aside from blood oxygen concentration, the concentration of other components such as lipids may be computed. The blood vessels are not a limitation, and the concentration of the lymph fluid component in a lymph duct may be measured and computed. It is also possible to measure and compute the concentration of the cerebrospinal fluid component. The component measurement apparatus 1 also may be used to test animals other than humans. Aside from animals, the component measurement apparatus 1 also may be used for the measurement of the liquid components or concentrations in plants such as fruits.

Variation 2

In the foregoing First Embodiment, the direct mechanism comprised of the motor 42, the threaded rod 43, and the nut 44 is used to move the calibration plate 21 between the block position 45 and the storage position 46. However, the calibration plate 21 may be moved using other direct mechanisms. The direct mechanism may use an air cylinder, linear motor, an ultrasonic motor, an electrostatic motor, a crank mechanism, or a cam mechanism. The calibration plate 21 may be rotated to move between the block position 45 and the storage position 46. The calibration plate 21 also can be moved between the block position 45 and the storage position 46 using these members. These can make structures that are easy to produce. The motor 42, the threaded rod 43, and the nut 44 may be removed from the calibration unit 14, and a handle may be provided for the calibration plate 21. The calibration plate 21 can then be moved by the subject 2. This can extend the life of the rechargeable battery 24.

Variation 3

In the foregoing First Embodiment, the calibration plate measurement step (step S2) and the object measurement step (step S3) are continuously performed. However, the object measurement step (step S3) may be performed more frequently than the calibration plate measurement step (step S2). In this way, the period of the object measurement step (step S3) can be reduced. The frequency ratio of the calibration plate measurement step (step S2) and the object measurement step (step S3) may be varied according to the measurement result of the object measurement step (step S3). Specifically, the object measurement step (step S3) may be performed more frequently when the glucose concentration is abnormal than when the glucose concentration is normal. In this way, glucose concentration changes can be measured in greater detail in an abnormal state.

Variation 4

In the foregoing First Embodiment, the light-emitting devices 27 are installed in the sensor module 12. However, the light-emitting devices 27 may be excluded from the sensor module 12, and the measurement light 31 may be applied to the measured portion 2a from a light source different from the light-emitting devices 27. Because the light-emitting devices 27 are absent, the sensor module 12 can be produced with improved productivity.

Variation 5

In the foregoing Second Embodiment, steps S12 to S32 are performed once before step S14. However, step S14 may be performed after performing steps S12 to S32 multiple times. In this way, the voltage data corresponding to the first reflected light 32a can more accurately approach the reference value.

Variation 6

In the foregoing Second Embodiment, the input voltage signal to the first amplifier 94 from the first D/A converter 93 is varied. However, it is also possible to vary the gain of the first amplifier 94, as in Third Embodiment. The light intensity of the measurement light 31 can also be varied in this manner.

Variation 7

In the foregoing Second Embodiment, the applied voltage to the light-emitting devices 27 is varied. In the foregoing Third Embodiment, the gain of the second amplifier 102 is varied. However, it is also possible to vary both the applied voltage to the light-emitting devices 27, and the gain of the second amplifier 102. With a wider variable range, the device life can be extended when changes occur over time.

The entire disclosure of Japanese Patent Application No. 2015-029301 filed on Feb. 18, 2015 is hereby incorporated herein by reference.

What is claimed is:

1. An information acquisition apparatus comprising:
   a photoreceiver that receives second reflected light, the second reflected light being provided by reflecting source light off of an object, the photoreceiver being configured to output a second signal corresponding to second light intensity of the second reflected light;
   a calibrator having a stable reflectance that outputs first reflected light to the photoreceiver, the photoreceiver being configured to output a first signal corresponding to first light intensity of the first reflected light, the first reflected light being provided by reflecting the source light off of the calibrator, the first reflected light being used for comparing the first and second light intensities; and a switcher that is provided between the photoreceiver and the object, the calibrator being slidable along an inner surface of the switcher so as to provide first and second states by selectively blocking the source light from reaching the object, wherein, in the first state, the source light reaches the object to form the second reflected light that is received by the photoreceiver, and wherein, in the second state, the source light is blocked by the calibrator so that the source light is reflected by the calibrator to form the first reflected light that is received by the photoreceiver.

2. The information acquisition apparatus according to claim 1, wherein in the first state, the calibrator is located at a storage position where a light path of the second reflected light is not blocked.

3. The information acquisition apparatus according to claim 1, wherein in the second state, the calibrator is located at a blocking position where a light path of the second reflected light is blocked.

4. The information acquisition apparatus according to claim 1, further comprising a calibration arithmetic section that calibrates second light intensity of the second reflected light based on the first light intensity of the first reflected light.

5. The information acquisition apparatus according to claim 1, wherein the photoreceiver includes:
a light-emitting device that emits the source light selectively applied to the calibrator and the object; and
a light-receiving device that selectively receives the first reflected light and the second reflected light,
wherein the light-emitting device and the light-receiving device have optical axes in a same direction.

6. The information acquisition apparatus according to claim 1, wherein the calibrator contains polytetrafluoroethylene.

7. The information acquisition apparatus according to claim 1, further comprising a control section configured to slide the calibrator along the inner surface of the switcher so as to switch an input light incident to the photoreceiver between the first reflected light and the second reflected light.

8. An information acquisition method for causing a processor to execute computer-readable instructions stored in a memory, the method comprising executing the computer-readable instructions on the processor the steps of:

installing an information acquisition apparatus on an object, the information acquisition apparatus having a calibrator and a switcher;

selectively moving the calibrator along an inner surface of the switcher so as to provide blocking and storage states by selectively blocking source light from reaching the object;

applying the source light to the calibrator so as to detect first light intensity of first reflected light, the first reflected light being obtained by reflecting the source light off of the calibrator after the calibrator has slid along the inner surface of the switcher to a blocking position in the block state;

applying the source light to the object so as to detect second light intensity of second reflected light, the second reflected light being obtained by reflecting the source light off of the object after the calibrator has slid along the inner surface of the switcher to a storage position in the storage state;

acquiring information of the object using the first light intensity of the first reflected light and the second light intensity of the second reflected light; and repeating the detection of the first light intensity of the first reflected light, the detection of the second light intensity of the second reflected light, and the acquisition of the information of the object while the information acquisition apparatus is being installed on the object.

* * * * *